US006266645B1

(12) United States Patent
Simpson

(10) Patent No.: US 6,266,645 B1
(45) Date of Patent: Jul. 24, 2001

(54) RISK ADJUSTMENT TOOLS FOR ANALYZING PATIENT ELECTRONIC DISCHARGE RECORDS

(75) Inventor: Kit N. Simpson, Alameda, CA (US)

(73) Assignee: iMetrikus, Inc., Carlsbad, CA (US)

( * ) Notice: Subject to any disclaimer, the term of this patent is extended or adjusted under 35 U.S.C. 154(b) by 0 days.

(21) Appl. No.: 09/145,943

(22) Filed: Sep. 1, 1998

(51) Int. Cl.[7] .................................................. G06F 17/60
(52) U.S. Cl. ........................................................ 705/3
(58) Field of Search ....................................... 705/2, 3, 4

(56) References Cited

U.S. PATENT DOCUMENTS

| | | | | |
|---|---|---|---|---|
| 4,667,292 | * | 5/1987 | Mohlenbrock et al. | 364/406 |
| 5,018,067 | * | 5/1991 | Mohlenbrock et al. | 364/413.02 |
| 5,724,379 | * | 3/1998 | Perkins et al. | 395/202 |
| 5,778,345 | * | 7/1998 | McCartney | 705/2 |
| 5,835,897 | * | 11/1998 | Dang | 705/2 |
| 5,845,254 | * | 12/1998 | Lockwood et al. | 705/2 |
| 5,915,241 | * | 6/1999 | Giannini | 705/2 |

OTHER PUBLICATIONS

Fowles, Jinnet B. et al., "Taking Health Status Into Account When Setting Capitation Rates: A Comparison of Risk–Adjustment Methods", Journal of the American Medical Association (JAMA), vol. 276, No. 16, p. 1316 (start page), Oct. 1996.*

Ellis, Randall P. et al., "Diagnosis–Based Risk Adjustment for Medicare Capitation Payments", Health Care Financing Review, vol. 17, No. 3, p. 101 (start page), Spring 1996.*

Weiner, Jonathan P. et al., "Risk–Adjusted Medicare Capitation Rates Using Ambulatory and Inpatient Diagnoses", Health Care Financing Review, vol. 17, No. 3, p. 77 (start page), Spring 1996.*

Members of the American College of Chest Physicians/Society of Critical Care Medicine Consensus Conference Committee, "American College of Chest Physicians/Society of Critical Care Medicine Consenus Conference: Definitions for Sepsis and Organ Failure and Guidelines for the Use of Innovative Therapies in Sepsis," vol. 20, pp. 864–874, Jun. 1992, *Critical Care Medicine*.

Lee, et al., "Risk Adjustment, A Special Report: A Key to Changing Incentives in the Health Insurance Market," Mar. 1997, pp. 3–26, *Alpha Center*.

Michael Shwartz, et al., "The Importance of Comorbidities in Explaining Differences in Patient Costs," 1996, vol. 34, pp. 767–782, *Medical Care*.

* cited by examiner

Primary Examiner—Eric W. Stamber
Assistant Examiner—Susanna Meinecke-Díaz
(74) Attorney, Agent, or Firm—Beyer Weaver & Thomas LLP

(57) ABSTRACT

A system and method are disclosed for examining and effectively managing resource allocation in a health care organization or facility (e.g., a hospital, a hospice, or a nursing home). The disclosed technology relies upon an analysis of the electronic discharge records of a health care organization in a manner that allows extraction of only those records that were generated for patients having a specified condition (e.g., septic shock, coronary artery disease, autoimmune disease, etc.) or fall into a particular class based upon resource usage (e.g., length of hospital stay, type of surgery, or quantity and type of pharmaceuticals taken). Note that discharge records often fail to explicitly specify the condition of interest. To accomplish selective extraction, the content of the discharge records is matched against one or more "key explanatory variables" such as a "selection vector" which is collection of patient codes that implicitly specify the condition of interest.

20 Claims, 12 Drawing Sheets

Figure 1B

| Description | Code | Units | Total Charges |
|---|---|---|---|
| ROOM-BOARD/SEMI | 120 | 7 | 2898:00 |
| PHARMACY | 250 | 52 | 78:28 |
| IV SOLUTIONS | 258 | 14 | 119:70 |
| DRUGS/OTHER INJ | 259 | 19 | 337:45 |
| MED/SUR SUPPLIES | 270 | 79 | 2411:90 |
| SUPPLY/IMPLANT | 278 | 4 | 7794:35 |
| LABORATORY | 300 | 1 | 59:00 |
| LAB/CHEMISTRY | 301 | 2 | 176:70 |
| LAB/HEMOTOLOGY | 305 | 10 | 203:80 |
| LAB/BACT-MICRO | 306 | 2 | 105:15 |
| OPERATING ROOM | 360 | 11 | 2241:00 |
| BLOOD/ADMIN | 391 | 1 | 27:00 |
| RESPIRATORY SVC | 410 | 3 | 22:80 |
| PHYSICAL THERP | 420 | 10 | 656:10 |
| RECOVERY ROOM | 710 | 1 | 168:75 |
| TREATMENT/OBV. RM | 760 | 2 | 74:90 |
| TOTAL | 001 | | 17374:88 |

Birth Date: 4/04/13

Room-Board/Semi charge: 414 00

| Payer | Deductible |
|---|---|
| Medicare part A and Part Physicians Mutual | 376:00 |

Insured's info:
- F 01 517163071A MED SUPP
- F 01 000706032

Employer Name: RETIRED / RETIRED (A 9 / B 9)

Principle and other diagnoses descriptions: OSTEROARTHROS NOS-L/LEG
Prin CODE: 71596    Other Diagnoses Codes: 9975, 0417

Principal and other procedure descriptions: 9 TOTAL KNEE RPLCMENT
Principal Procedure CD: 8154  Date: 10/12

App From: 5

| Variable | Parameter Estimate | Standard Error | T for HO: Parameter=0 | Prob >\|T\| |
|---|---|---|---|---|
| INTERCEPT | -10.22 | 190.26 | -0.054 | 0.9572 |
| PRIME VECTOR | -1955.38 | 400.95 | -4.877 | 0.0001 |
| SPEC. UNIT | 3714.07 | 273.13 | 13.598 | 0.0001 |
| SURGERY | 3298.07 | 599.70 | 5.500 | 0.0001 |
| DIED | -411.54 | 233.08 | -1.766 | 0.0775 |
| BEDS 199 | 1726.11 | 275.06 | 6.275 | 0.0001 |
| BEDS 299 | 1027.92 | 213.44 | 4.816 | 0.0001 |
| BEDS 500 | -422.92 | 229.68 | -1.841 | 0.0656 |
| NORTHEAST | 3406.36 | 290.05 | -11.744 | 0.0001 |
| NORTH-CENTRAL | -2322.27 | 199.47 | -11.642 | 0.0001 |
| GRAM STAIN | 730.13 | 132.91 | 5.494 | 0.0001 |
| TRANSFUSION CROSS-MATCH | 481.72 | 38.40 | 12.546 | 0.0001 |
| CHEMISTRY PANEL 12 | 261.48 | 64.79 | 4.036 | 0.0001 |
| UNSPECIFIED LAB TEST | 535.47 | 36.79 | 14.554 | 0.0001 |

*FIG. 5A*

| Variable | Parameter Estimate | Standard Error | T for HO: Parameter=0 | Prob >|T| |
|---|---|---|---|---|
| URINARY MICROSCOPY | -563.99 | 128.54 | -4.388 | 0.0001 |
| UNSPECIFIED BACTERIA TEST | 188.54 | 76.53 | 2.464 | 0.0138 |
| SERUM MAGNESIUM | 462.60 | 44.33 | 10.436 | 0.0001 |
| BACTERIAL SENSITIVITY | 217.54 | 80.12 | 2.715 | 0.0066 |
| RANDOM GLUCLOSE | 92.25 | 6.41 | 14.383 | 0.0001 |
| A.P.P.T | 516.35 | 41.46 | 12.455 | 0.0001 |
| MIC** | 426.34 | 70.33 | 6.062 | 0.0001 |
| BLOOD GASES | 603.28 | 28.53 | 21.148 | 0.0001 |
| LEUKOCYTE DIFFERENTIAL | 375.33 | 31.01 | 12.104 | 0.0001 |
| CHEMISTRY PANEL 7 | 657.81 | 30.87 | 21.310 | 0.0001 |
| SPECIMEN COLLECTION | 102.20 | 11.74 | 8.702 | 0.0001 |
| AEROBIC/ANAEROBIC BACTERIAL CULTURE | 994.68 | 45.63 | 21.797 | 0.0001 |
| AEROBIC CULTURE | 497.68 | 64.18 | 7.757 | 0.0001 |
| BLOOD COUNT (CBC) | 1001.97 | 26.24 | 38.189 | 0.0001 |

*FIG. 5B*

RISK ADJUSTMENT TOOLS FOR ANALYZING PATIENT ELECTRONIC DISCHARGE RECORDS

COPYRIGHT NOTICE

A portion of the disclosure of this patent document contains material which is subject to copyright protection. The copyright owner has no objection to the xerographic reproduction by anyone of the patent document or the patent disclosure in exactly the form it appears in the Patent and Trademark Office patent file or records, but otherwise reserves all copyright rights whatsoever.

BACKGROUND OF THE INVENTION

Generally, the present invention relates to computerized systems and methods for analyzing hospital electronic discharge data to accurately predict the resources required to treat a patient. Further, the present invention relates to computerized systems and methods applied to such electronic discharge data to allow statistical patient classification based upon certain key explanatory variables of a patient's condition.

In the age of managed health care and government medical care programs (e.g., Medicare in the US), it has become increasingly important for hospitals or other patient care institutions to accurately monitor their costs and justify their treatment procedures. Hospitals contract with HMO's (health maintenance organizations) and other managed care providers to provide services for the patients enrolled by the HMO. HMOs contract with employers to enroll employees in their health care plans.

If two hospitals are vying for a contract from the same HMO, the hospital having a lower cost per patient should normally win such contract—all other features being equal. However, the cost differential may not necessarily be due to inefficiencies in the higher cost hospital. It may simply be that the higher cost hospital is treating, on average, sicker patients or patients requiring more care. If the managed health care provider can be made to understand this, it may actually decide to contract with the higher cost hospital. Similarly, when a managed health care provider is contracting with an employer, the health care organization may wish to charge some employers more than others to enroll their employees. This can be justified if the employer has a class of employees that are, on average, likely to be sicker or require more care than the employees of some other employer. Obviously, the health care provider must convince the employer that it is charging a higher premium for that employer's employees because they are actually more of a high cost risk. Unfortunately, no precise mechanism exists for this purpose—although a measure known as a "DRG" has been applied.

In the mid-1980's, the United States began, through it's Medicare program, to reimburse hospitals and other health care institutions a fixed dollar amount based upon a "diagnosis related group" (DRG) determined from certain medical conditions recorded by the hospital or organization attending to the patient. This practice has spread beyond the government and throughout the industry to HMOs, PPOs, etc. Each DRG classification is comprised of one or more codes (e.g., "ICD-9 codes" currently used in the US as specified in the International Classification of Disease, 9th Revision, Clinical Modification) each of which represents a specific medical condition. For example, ICD-9 code 42.0 represents a patient that is HIV positive, ICD-9 code 789.59 represents a patient which has septic shock, ICD-9 code 410.9 represents a patient who had a myocardial infarction. All told, there are several thousand such ICD-9 codes.

Obviously, a hospital must properly identify the ICD-9 codes for each of its patients. Hospitals now have internal staff groups (medical records librarians) whose sole function is to identify proper ICD-9 codes and input them into patient records. To do this, such hospital financial staff groups take the clinical records provided by the physicians and nurses attending to a patient and attempt to determine which ICD-9 codes fit with the clinical records available to them. The hospital financial group then inputs a collection of ICD-9 codes in a standard electronic form (a "UB-92" form in the US). These and similar forms will often be referred to herein generically as hospital or health care "electronic discharge records."

The codes are entered in a specified order (e.g., the first ICD-9 code represents the principal condition for which the patient was treated, and subsequent ICD-9 codes may represent the conditions present at the hospital admission and other conditions that develop during the patient's stay). In the US, the codes are entered pursuant to a protocol specified by The Health Care Financing Agency ("HCFA"). The electronically formatted ICD-9 codes (together with other demographic information) for each patient are then used to classify patients into particular DRGs. A specific protocol governs DRG classification; for example, the principal diagnostic code, the presence of comorbidity conditions, the patient's age, the use of surgical procedures, and death or survival together dictate the DRG classification.

Unfortunately, there is considerable variance in costs for treating all those patients falling within a specific DRG. This is because DRGs do not do a particularly good job of classifying patients with sufficient specificity. For example, a DRG associated with a particular condition may provide reimbursement at a rate of $100,000 per patient. However, within the class of patients meeting this DRG, some may only cost the hospital $50,000 while others may cost the hospital $500,000 or more. Obviously, if one hospital has more than its share of patients falling within the DRG category for the particular condition and yet costing well in excess of the approximately $25,000 average charge, the hospital would like to be able to explain its additional costs.

The problem is exacerbated because the medical records librarians responsible for entering the ICD-9 codes and other information frequently fail to enter those codes that directly specify patient conditions. For example, ICD-9 code 038.9 specifies that a patient has sepsis. However, analysis of a large sample of UB-92 records has shown that only 27 percent of all sepsis patients actually have had code 038.9 recorded. Obviously, it is therefore not possible to identify all patients having sepsis (or most any other serious condition for that matter) by simply analyzing a hospital's electronic discharge records (e.g., the UB-92 records). This problem arises in part because of the large number of codes and the associated complexity of the ICD-9 code system. It also arises in part because the poor linking between a hospital's clinical production system (discharge summaries, doctors and nurses notes, etc.) and its financial billing system (ICD-9 coded records).

To address these and other issues, some "risk adjustment tools" have been developed. In some cases, these attempt to explain the statistical variance in cost of treating the patients falling under a particular DRG (or other generic patient classification). Early risk adjustment tools were simple models used by insurance companies for health insurance underwriting and pricing individual premiums. More sophisticated modern tools were developed by deploying powerful statistical software to analyze patient databases and identify patterns in patient records. These tools were then provided as software to gauge risk within certain patient populations.

All risk adjustment tools model some combination of demographic and/or health status data. See "Risk Adjustment" by C. Lee and D. Rogal, produced for The Robert Wood Johnson Foundation, March 1997. Demographic models generally include some or all of the following variables: age, sex, family status, geographic location, and welfare status. Measures of health status can include survey data of health, diagnoses, and data reflecting prior utilization. Health status models may include demographic variables as predictors of health.

Some more recent risk adjustment tools employ ICD-9 codes to classify patients. See the above-referenced "Risk Adjustment" paper, pages 14–15. Unfortunately, the best of the existing tools typically can explain no more than about 45 percent of the variance in patient cost within a given DRG. This leaves over 50 percent of the variance unexplained. In addition, known risk adjustment tools were developed using fairly narrow databases, and therefore predict best for a specific population group or health care setting.

In view of the above, medical records analysis technology could be improved to provide a method for ascribing the variance within a generic class of patients (such as all patients grouped into the DRG for particular patient condition category).

SUMMARY OF THE INVENTION

This invention provides technology for identifying effective resource allocation in a health care organization or facility (e.g., a hospital, hospice, or nursing home). The technology is based upon a statistical analysis of health care data in a manner that allows extraction of "key explanatory variables" such as "selection vectors" that select the electronic discharge records of only those patients that have a specified condition (e.g., septic shock, coronary artery disease, auto-immune diseases, red blood cell disorders, leukemias, chirrosis, chest pain, adult diabetes, etc.) or fall into a particular class based upon resource usage (e.g., length of hospital stay, type of surgery, or quantity and type of pharmaceuticals taken).

Various types of "key explanatory variables" may be employed to analyze the electronic "discharge records" of health care organizations. The key explanatory variables correspond to one or more pieces of information, contained in electronic discharge records such as UB-92 records described above, which record some specific event or condition associated with the patient. Common to all key explanatory variables is a disproportionately large impact on resource usage or a strong indication of a resource intensive medical condition. Further all key explanatory variables are premised upon the identification of a particular condition that may not be immediately apparent from inspection of any given electronic discharge record or other electronic hospital record. For example, very often the medical condition sepsis or septic shock is not specifically identified in the electronic discharge records of a given patient. Certain key explanatory variables are identified based upon a statistically significant correlation between sepsis (preferably high resource usage cases of sepsis) and specific information contained in patient electronic discharge records.

One example of a key explanatory variable is a "selection vector" listing one or more "patient condition codes" (e.g., ICD-9 codes) which together implicitly specify a condition such as septic shock. An example of a selection vector for the medical condition septic shock may specify patient condition codes for (1) failure of a major system such as the renal system or the cardiovascular system and (2) infection of an organ or organ system outside the system which has failed.

Another key explanatory variable is a "laboratory cost driver" corresponding to a laboratory test which when performed on the patient indicates a very large (disproportionate) effect on resource usage. Information as to whether or not such a laboratory test was conducted (and how many such tests were conducted) typically resides in certain electronic records for patients of a health care organization. Note that the UB-92 discharge record format described above typically does not specify laboratory test information in detail, so other types records may have to be evaluated to identify laboratory cost drivers.

In one example, the use of an anaerobic bacterial culture test (sometimes indicating a suspicion of sepsis) costs less than approximately $100, but is shown by statistical analysis to be associated with an additional patient cost of about $1,000. Further, each additional anaerobic bacterial culture test adds about another $1,000 to the cost of treating the patient.

From the selection vectors, laboratory cost drivers, and other key explanatory variables associated with a particular condition, an expression can be developed for predicting the resource usage required for various patients. By applying this expression to the electronic discharge records (and other appropriate records if necessary) for a group of patients, the patients can be classified according to whether they have a particular condition and how much resource usage should be expected with their treatment.

The statistical information obtained in accordance with this invention may be employed for various purposes. For example, it may be employed in a risk adjustment computer software tool to accurately classify patients based upon conditions which require differential resource usage. Preferably, the classification has greater granularity than the DRG classification used for reimbursement purposes. That is, it subdivides a given DRG into multiple classifications by risk of death and cost. This allows a comparison of outcomes and costs across organizations for purposes of quality and cost management. Note that it is possible that a given subdivision may straddle more than one DRG.

The tools of this invention may also be employed to help define specific guidelines for treatment of patients. Patients falling into specific risk classifications, when subject to the analysis of this invention, may have certain conditions that could not otherwise be previously identified from the electronic discharge records. Guidelines to make more efficient use of available resources could then be specifically developed for the condition at issue.

Still further, the invention may be employed to determine whether new or existing guidelines are being followed. Because the invention accurately predicts resource usage for a certain set of conditions (and for following guidelines for those conditions), it may be employed to determine whether a health care organization is using more resources than expected. If so, it is likely that the staff is not following the guidelines in a large proportion of the cases.

These and other features and advantages of the invention will be described in more detail below with reference to the associated drawings.

BRIEF DESCRIPTION OF THE DRAWINGS

FIG. 1B is a depiction of a hospital electronic discharge record that may be processed by computer systems and methods of this invention.

FIGS. 5A and 5B together are a list of terms for a linear expression incorporating a selection vector, various laboratory cost drivers, and other key explanatory variables to predict the total cost of a hospital admission.

DETAILED DESCRIPTION OF THE PREFERRED EMBODIMENTS

Figure 1A:
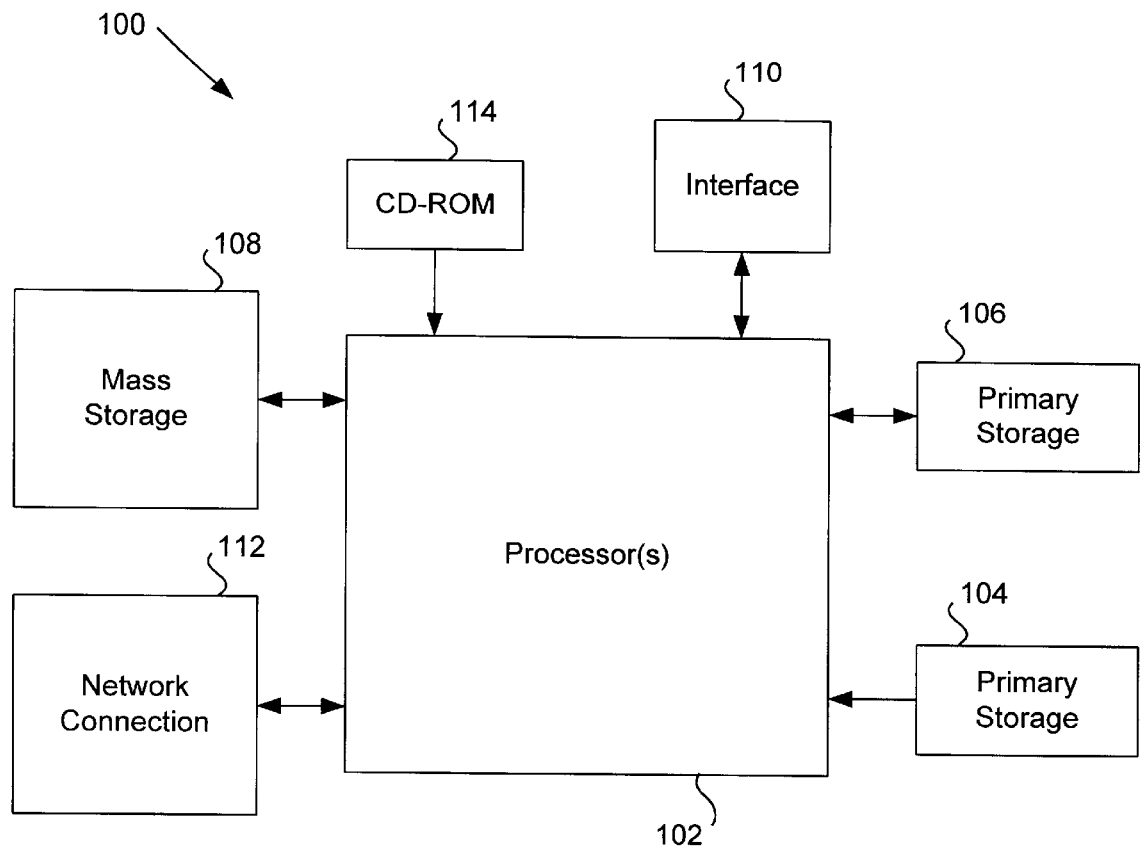
FIG. 1A is a block diagram of a generic computer system useful for implementing the present invention.

The present invention provides methods and systems for analyzing electronic discharge records of patients in order to classify the patients according to a specified underlying condition that is not necessarily reflected in data elements in the discharge records. Further, the invention predicts or models resource usage by specific patients having a specified underlying condition. In the following description, various specific details are set forth in order to fully illustrate preferred embodiments for accomplishing the classification and modeling of this invention. For example, certain specific applications of the invention (e.g., identifying patients who had septic shock and modeling the cost of their treatment) will be described. It will be apparent, however, that the invention may be practiced without limitation to the specific details and applications presented herein.

DEFINITIONS

Some of the terms used herein are not commonly used in the art. Other terms are used in the art but not necessarily consistently. Therefore, the following definitions are provided as an aid to understanding the description that follows. The invention as set forth in the claims should not strictly be limited by these definitions.

The term "health care organization" refers to any organization which treats or manages patients. Examples of health care organizations include hospitals, health maintenance or other capitated payment organizations, preferred provider organizations, hospices, nursing homes, home care businesses, etc. For purposes of this invention, the health care organization or some associated entity will generate electronic records of the patients for financial management or billing purposes.

The term "patient resources" refers to resources used to treat a patient while that patient is under the care of a health care organization. In the context of a hospital, patient resources may include a cost component of a patient's treatment, the type of room a patient occupies (e.g., room size, attendant facilities, etc.), the length of time the patient stays in the hospital, the type of surgery, if any, required, the types and quantities of pharmaceuticals taken, the types and numbers of tests employed, etc. If the health care organization is a capitated payment organization, patient resources may also include such items as the number and type of nurse visits, special equipment, etc. The term "electronic discharge records" or "patient electronic profile" refers to those records maintained by a hospital or other health care organization for the purpose of accounting, reimbursement, comparison to other health care organizations, or a similar purpose. Such records are readable by computer systems, and particularly those systems deploying software that reads and analyzes such records. Often, such records contain multiple fields, each designated for entry of one or more ICD-9 codes or other patient condition codes. An example of one such record is a UB-92 record illustrated in FIG. 1B. Another example of such record is an ICCS code record maintained by Commission of Professional and Hospital Associations ("CPHA") which records the particular laboratory tests that were used to treat a patient. Of course, the present invention may utilize other forms and formats which recite patient condition codes, laboratory related cost drivers, or other information having a strong statistical correlation to resource usage and/or outcomes.

The term "key explanatory variable" is used herein to refer to any indicator which, when applied to a health care organization's electronic discharge records, will select those records associated with patients having a particular condition, a specified level of resource usage and/or a specified medical outcome. Examples include selection vectors of ICD-9 codes, laboratory cost drivers corresponding to tests performed on the patient, the geographic region within the country where the patient was treated, the number of beds or rooms in the health care organization, whether or not the patient died, whether or not surgery was required, whether or not the patient stayed in the intensive care unit, etc.

A "patient condition code" refers to a code employed to specify a patient condition for entry in an electronic discharge record. The code may take the form of a text string or a numerical string or other appropriate format. Patient condition codes are typically specified by a government agency or other large organization. Often, such codes are provided for the purpose of calculating or determining a reimbursement level to a health care organization for a particular patient. Examples of patient condition codes include DRG codes, ICCS codes, ICD-8 codes, ICD-9 codes, ICD-10 codes, CPT-4 codes, etc. The ICD-9 codes are presented in "ICD-9.CM," Fifth Edition, International Classification of Diseases, 9th Revision, Clinical Modifications, McGraw-Hill, Inc., New York, N.Y. (1996) and CPT-4 codes are presented in "AMA Physicians' Current Procedural Terminology CPT 97," CPT Intellectual Property Series, Chicago, Ill., 1996, both of which are incorporated herein by reference for all purposes.

COMPUTER SYSTEMS FOR IMPLEMENTING THE INVENTION

Embodiments of the present invention as described herein employ various process steps involving data stored in or transferred through computer systems. The manipulations performed in implementing this invention are often referred to in terms such as identifying, selecting, or comparing. Any such terms describing the operation of this invention are machine operations. Useful machines for performing the operations of embodiments of the present invention include general or special purpose digital computers or other similar devices. In all cases, there is a distinction between the method of operations in operating a computer and the method of computation itself. Embodiments of the present invention relate to method steps for operating a computer in processing electrical or other physical signals to generate other desired physical signals.

Embodiments of the present invention also relate to an apparatus for performing these operations. This apparatus may be specially constructed for the required purposes, or it may be a general purpose computer selectively activated or reconfigured by a computer program and/or data structure stored in the computer. The processes presented herein are not inherently related to any particular computer or other apparatus. In particular, various general purpose machines may be used with programs written in accordance with the teachings herein, or it may be more convenient to construct a more specialized apparatus to perform the required method steps. The required structure for a variety of these machines will appear from the description given below.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

FIG. 1A illustrates a typical computer system in accordance with an embodiment of the present invention. The computer system 100 includes any number of processors 102 (also referred to as central processing units, or CPUs) that are coupled to storage devices including primary storage 106 (typically a random access memory, or RAM), primary storage 104 (typically a read only memory, or ROM). As is well known in the art, primary storage 104 acts to transfer data and instructions uni-directionally to the CPU and primary storage 106 is used typically to transfer data and instructions in a bi-directional manner Both of these primary storage devices may include any suitable computer-readable media such as those described above. A mass storage device 108 is also coupled bi-directionally to CPU 102 and provides additional data storage capacity and may include any of the computer-readable media described above. Mass storage device 108 may be used to store programs, data and the like and is typically a secondary storage medium such as a hard disk that is slower than primary storage. It will be appreciated that the information retained within the mass storage device 108, may, in appropriate cases, be incorporated in standard fashion as part of primary storage 106 as virtual memory. A specific mass storage device such as a CD-ROM 114 may also pass data uni-directionally to the CPU.

CPU 102 is also coupled to an interface 110 that includes one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 102 optionally may be coupled to a computer or telecommunications network using a network connection as shown generally at 112. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for matching selection vectors to patient electronic profiles (in electronic discharge records for example) may be stored on mass storage device 108 or 114 and executed on CPU 108 in conjunction with primary memory 106.

A computer system such as system 100 typically analyzes electronic discharge records or other appropriate patient electronic profiles when operated in accordance with this invention. Such records may be stored on a machine readable medium such as devices 108 or 114 and analyzed by CPU 108 in conjunction with primary memory 106. FIG. 1B depicts some important features of a UB-92 (HCFA-1450) form 150 which is a standard electronic discharge record. UB-92 forms are conventionally required for Medicare reimbursement. For each patient treated by a health care organization, a medical records librarian reviews the patient's clinical records (as provided by an attending health care professional such as a doctor) and fills out a UB-92 form. The organization then submits the completed form to Medicare or other entity for reimbursement. As mentioned, the reimbursement level depends upon classification of the treatment into an appropriate DRG based upon analysis of the UB-92 form.

Form 150 includes various fields for medical records librarians to enter pertinent information chronicling a patient's treatment. Within form 150, a section 152 contains fields for various pieces of generic patient information such as name, address, birthdate, sex. It also includes less generic information which is specific to the patient's treatment such as a patient control number, a federal tax number, and a date on which the condition occurred.

Also within electronic medical record 150, a section 154 provides a listing of various expenses actually incurred by the hospital in treating the patient. As shown in this example, there are entries for pharmacy products, medical/surgical supplies, various tests and laboratory supplies, physical therapy, and operating room usage. Each of these items includes a cost to the hospital. These costs are summed and provided in a "total" line in the UB-92 form. Note that Medicare (or other payer using the UB-92 form) does not reimburse the hospital based upon these costs.

A section 156 includes the various patient condition codes that the medical records librarians enter when analyzing clinical records for the patient's treatment. In general, UB-92 forms such as form 150 include fields for a minimum of five diagnosis codes (e.g., septic shock, cancer, etc.) and fields for a minimum of three codes for procedures (e.g., surgery). Some patient treatments are limited and therefore do not require all eight patient condition code sections to fully describe the treatment. Within section 156, a principal diagnostic code field 158 specifies the diagnosis which largely determines the reimbursement. And "other diagnostic codes" section 160 lists such auxiliary diagnoses as comorbidities. While not shown in FIG. 1B, one example might provide a principal diagnostic code of 038.40 (the ICD-9 code for gram negative septicemia) and secondary (other) codes including disseminated intervascular coagulation (ICD-9 286.6) and acute venticular failure (ICD-9 391.8).

Below the diagnostic codes sections, multiple procedure code sections are provided. A "principal procedure" code 162 is provided for the main procedure performed while the patient was being treated. An "other procedure" code section 154 is provided for auxiliary procedures.

SELECTION VECTORS AND LABORATORY COST DRIVERS AS KEY EXPLANATORY VARIABLES

As indicated above, one key explanatory variable is a selection vector specifying one or more encoded patient conditions which can be matched against electronic discharge records from a health care organization. The selection vector should be carefully chosen and preferably validated by, for example, a statistical analysis such as that set forth below. The resulting selection vector should extract only those records of patients having a specified medical condition for which the vector was designed. The specified medical condition selected by the selection vector may be septic shock or any of a number of other conditions. A partial listing of such conditions and associated DRG codes follows.

| DRG | Admissions Type |
| --- | --- |
| 76 & 77 | Other Resp Surg Complications or Comorbidities |
| 204 | Disorders of Pancreas |
| 277 & 278 | Cellulitus |
| 316 | Renal Failure |
| 144 & 145 | Other Circulatory Complications or Comorbidities |
| 15 | Transient Ischemic Attack and Precerebral Occlusion |
| 130 & 131 | Peripheral Vascular Accident Complications or Comorbidities |
| 294 & 295 | Diabetes Adult |
| 395 | Red Cell Disorders |
| 24 & 25 | Seizures, Headaches, Complications or Comorbidities |
| 403 & 404 | Lymphomas, Leukemias |
| 188 & 189 | Other Digestive Complications or Comorbidities |
| 202 | Chirrosis, Hepatitis |
| 127 | Heart failure with Shock |
| 475 | Respiratory Involvement with Ventilator |
| 416 | Septicemia Adult |
| 121, 122 & 123 | Circulatory, Acute Myocardial Infarction |
| 79 & 80 | Respiratory Infection |
| 174 & 175 | Gastro-intestinal tract Hemorrhage |
| 488, 489 & 490 | HIV |
| 296 & 297 | Nutri-Metabolic |
| 182 & 183 | Esophagitis Complications or Comorbidities |
| 140 | Angina |
| 320 & 321 | Kidney Urinary Track Infection Complications or Comorbidities |
| 138 & 139 | Cardiac Arrhythmia Complications or Comorbidities |
| 143 | Chest Pain |

Again, the DRG codes are provided in the "DRG Guide," 1997 Ed., Medicode, Inc., Salt Lake City, Utah, 1996, which is incorporated herein by reference for all purposes.

Figure 2A:
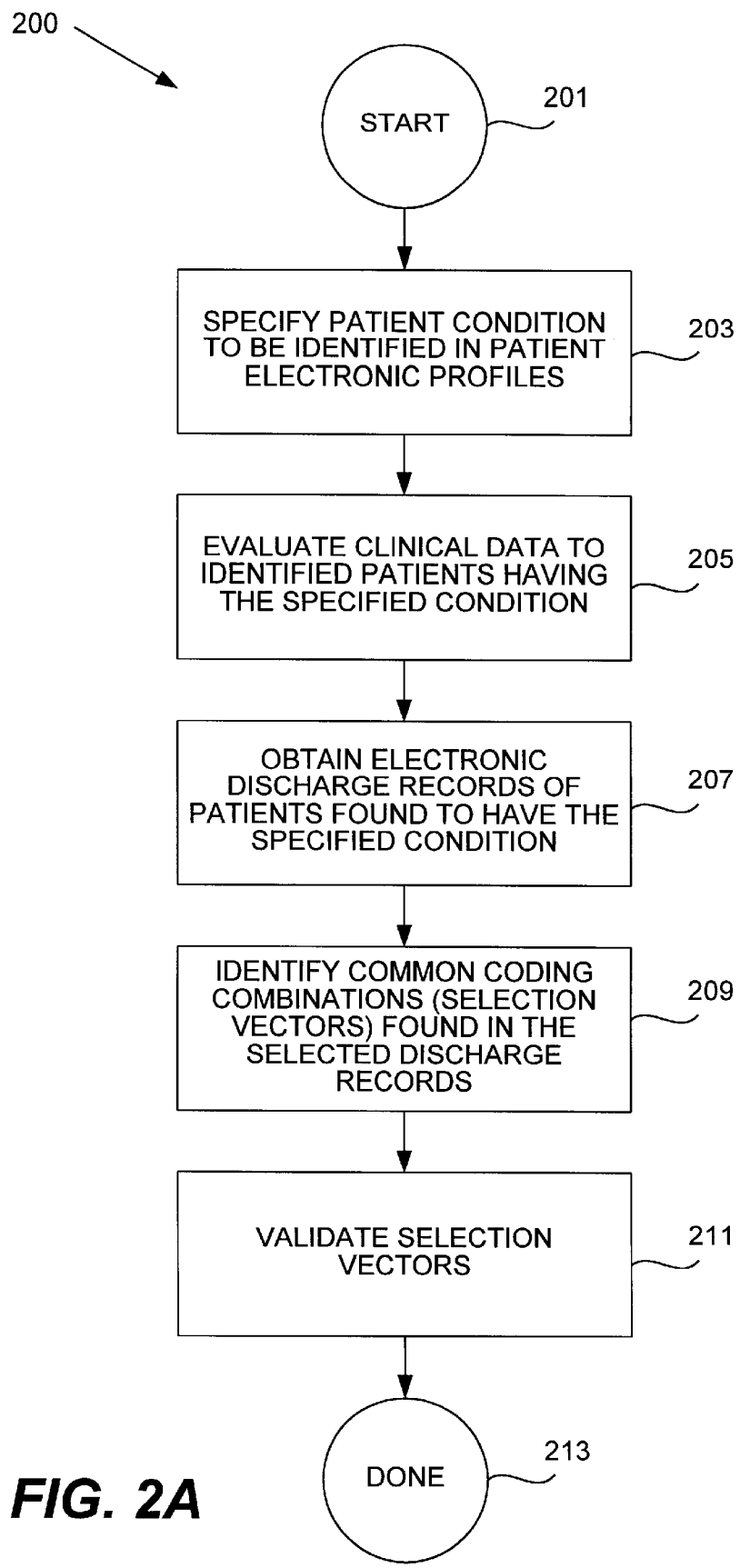
FIG. 2A is a process flow diagram depicting the steps employed to generate a selection vector in accordance with one preferred embodiment of this invention.

One approach to defining such selection vectors is set forth in FIG. 2A. As shown there, a process 200 begins at a starting point 201 and then specifies a patient condition to be analyzed in a step 203 (e.g., sepsis, HIV infection, liver cancer, toxemia, etc.). Next, a clinical data set is evaluated at a step 205 to identify a collection of patients that unambiguously have the condition of interest. Clinical data, which is not constrained by the limitations of a coding system such as the ICD-9 codes applied to UB-92 forms, should clearly identify those patients having a particular condition. Preferably, to provide a statistically significant sample, the clinical data set should represent at least about 100 patients.

Next, at a step 207, the electronic discharge records for those patients identified from the clinical data are provided for further analysis. Thus, one now has the electronic discharge records for a statistically significant sampling of patients known to have the condition of interest. These electronic records are analyzed to identify various coding combinations that they have in common. This produces one or more patient code combinations (selection vectors) specifying records for patients having the condition of interest. See step 209. This may not be a trivial task, given that thousands of different codes are available for entry into the electronic discharge records. When looking for a combination of codes, the likelihood that any particular combination will randomly occur is extremely small.

In a preferred embodiment, the selection vectors are generated after all patient condition codes in the electronic discharge records are ranked according to frequency of occurrence. The ranked list is then analyzed (automatically or manually) with physician guidelines available in the field. To generate vectors for sepsis or septic shock, one can employ guidelines provided in Bone et al., "American College of Chest Physicians/Society of Critical Care Medicine Consensus Conference: Definitions for sepsis and organ failure and guidelines for the use of innovative therapies in sepsis," Critical Care Medicine, 864–874, June 1992. The patient condition codes comprising the selection vectors can be generated from the list of codes in the clinical sample with the aid of a statistical technique such as analysis of variance, linear regression, logistic regression, CART (classification and regression trees), neural network techniques, entropy mini-max, and SMILES (similarity-metric least squares).

Obviously, if an electronic discharge record contains the exact code for the condition of interest, the problem is trivial. However, there is a need for the present invention partially because the code for the condition of interest frequently is not listed in the electronic discharge record. To ferret out those electronic discharge records that apply to patients having the condition of interest but do not list the code for the condition of interest, selection vectors having great specificity for the condition of interest are developed. When these are matched against the electronic discharge records, they should specifically select only those records for patients having the condition of interest.

Preferably, selection vectors of this invention have a sensitivity of at least about 80 percent (more preferably at least about 85 percent) and a specificity of at least about 70 percent (more preferably at least about 75 percent). This sensitivity and specificity have the meanings commonly used in statistics. Thus, a septic shock selection vector having a sensitivity of 86 percent, for example, will correctly select the electronic patient profiles of 86 out of every 100 septic shock patients. And, a septic shock selection vector having a specificity of 70 percent, for example, will not select the electronic profiles of 70 of every 100 sepsis patients; but it may select the profiles of 30 of these patients.

After the selection vectors have been selected based upon the analysis of the clinical data and the corresponding discharge records, those selection vectors should be validated by a statistically rigorous process. See step 211. Many such processes are known in the art. Generally, they will include a statistically significant sample of data unrelated to the data employed to generate the selection vectors. Examples of suitable validation techniques include analysis of variance, linear regression, logistic regression, probit and tobit modeling, CART (classification and regression trees), neural network techniques, entropy mini-max, and SMILES. The entropy mini-max process is described in Christensen, Ronald, "Entropy Minimax Multivariate Statistical Modeling-I: Theory," pages 231–277, and the SMILES process is described in U.S. patent application Ser. No. 08/784,206, filed on Jan. 15, 1997, naming Minor et al. as inventors, and entitled "METHOD AND APPARATUS FOR PREDICTING THERAPEUTIC OUTCOMES," both of which is incorporated herein by reference for all purposes. After the selection vector at issue has been validated, the process 200 is completed at a stopping point 213.

Typically, the chosen selection vectors are strings of one or more patient condition codes. In one preferred embodiment, the selection vector is simply a string of ICD-9 codes (numerals) covering the combination of interest. Any electronic discharge record found by matching to possess the same combination of patient condition codes is selected. Obviously, the format of the selection vector components should be the same as the format of the components of the electronic discharge record (e.g., key word strings, ICD-9 codes, etc.).

In a preferred embodiment, a match with a selection vector produced as described above not only indicates the presence of a condition but also specifies a limited range amount of additional resources that may be normally associated with that condition. Examples of the resources at issue include the length of stay at a health care facility, the type of facilities used by the patient (e.g., an intensive care unit), the costs of tests performed on the patient, the total cost of the patient's treatment, etc. By identifying the level of resource usage associated with patients having particular conditions, the selection vectors of the present invention can be employed to classify patients for risk adjustment, guideline monitoring, etc.

Another key explanatory variable of patient condition or expected resource allocation or medical outcome is the use of a particular laboratory test—termed a laboratory cost driver. Not surprisingly, laboratory cost drivers often turn out to be, from the clinical perspective, those tests that a typical physician would request to diagnose a condition that she suspects or to gauge the severity of a condition known to exist. Thus, the use of such tests (as indicated in an electronic record) strongly correlates with patient condition and resource usage.

While the choice of such laboratory cost drivers as key explanatory variables may seem logical in retrospect, only with rigorous statistical analysis of a large sample of data do some of these laboratory tests reveal themselves as key explanatory variables. To qualify as a key explanatory variable, the laboratory test should strongly correlate with a medical condition.

The laboratory cost drivers are chosen to strongly correlate with total resource usage for a given patient. In other words, when a patient record contains a laboratory cost driver, the total cost of treating the patient should typically deviate from the main by a significant amount. Often this amount will be far in excess of the true cost of the test that represents the laboratory cost driver. For example, the presence of a $50 test may have, on average, a $500 effect on the total cost of a patient's treatment.

From a mathematical perspective, a laboratory cost driver is preferably "statistically significant" (i.e., it maintains a p value of not more than about 0.05 in a regression test performed on a sample of about 100 admissions for a condition) and "economically meaningful" (i.e., it has a beta weight (parameter estimate) in regression of at least about three times the cost of the test itself). As illustrated below, the parameter estimate of laboratory cost driver may correspond to an expected change in the total cost of treating a patient each time the test associated with the cost driver is performed.

Figure 2B:
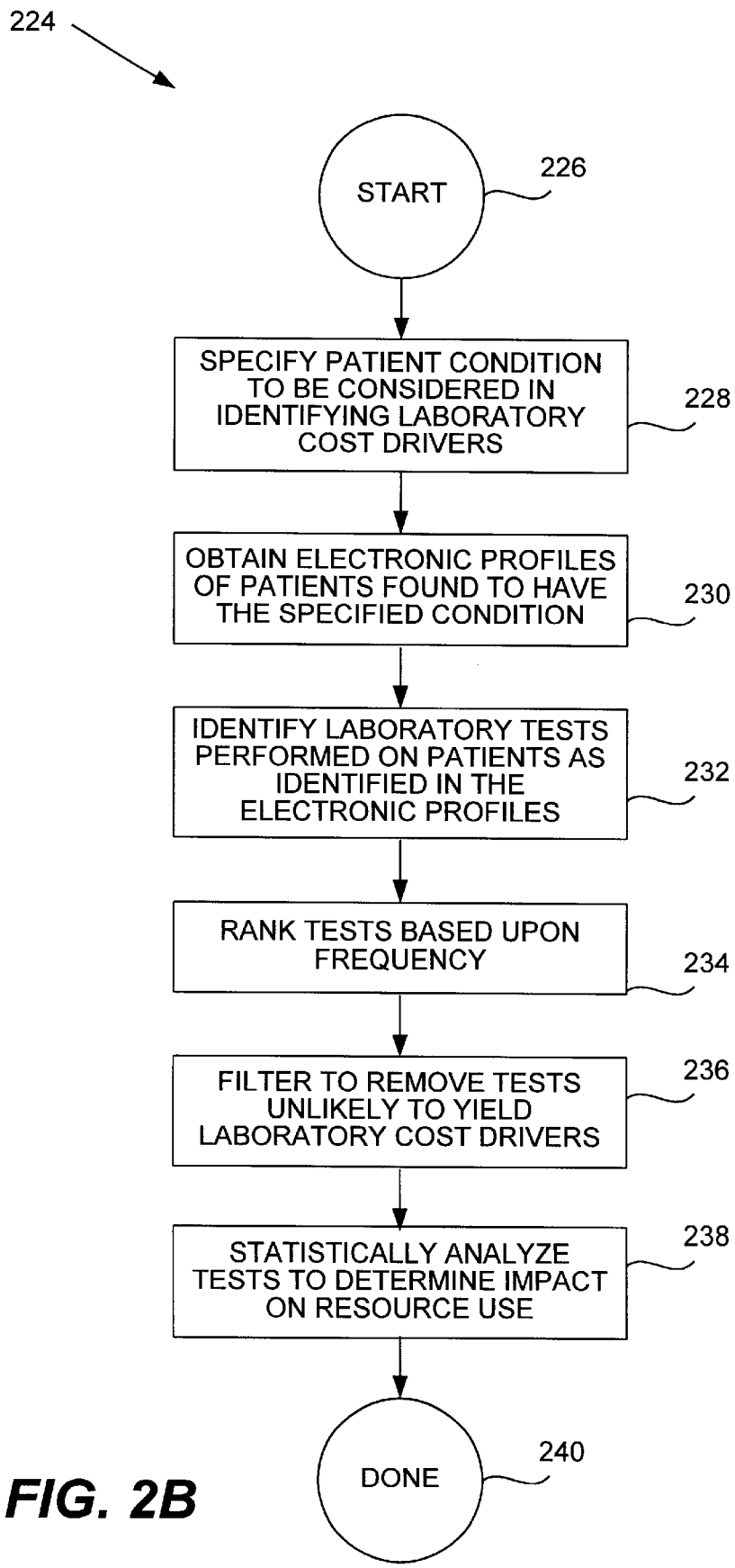
FIG. 2B is a process flow diagram depicting the steps employed to identify a laboratory cost driver in accordance with one preferred embodiment of this invention.

Referring now to FIG. 2B, a process 224 for identifying laboratory cost drivers is depicted. The process begins at a starting point 226, and then at a step 228 the condition from which the laboratory cost drivers are to be developed is specified. As mentioned, laboratory cost drivers may be identified by choosing them from a collection of electronic records for a patient having the pre-identified condition. To get at such records, one must first identify patients having the condition. This is accomplished at a step 230 by, for example matching the selection vectors described above with UB-92 forms for a number of patients. In another example, such records are obtained by selecting those records given the appropriate DRG for the condition of interest. The data set for the patients selected in step 230 may then be combined with the discharge records.

Regardless of how such records are obtained, they are now evaluated to identify and sum by test type all or at least many of the tests that were conducted for each patient in the data set. See step 232. Thereafter, the various tests are ranked by volume. Accordingly, the test that is performed more than all other tests is ranked first, the test that is performed second most often is ranked second, and so on. This is depicted in a step 234. Alternatively, the collection of such records is classified according total resource usage. For example, the records may be ranked according to the length of stay in a hospital, the total test costs, or the total administrative costs for the patients. Then, those records associated with patients who used up the most resources are separated for further analysis.

After the ranking, the tests may be filtered, as indicated in a step 236, to focus on those that most likely have a profound effect on resource usage. In one specific example, only the records associated with the top 10 percent of resource usage according to the selected resource category are selected. Also, the list may be analyzed to remove those tests that obviously have no relationship to the condition under consideration. For example, if the specified condition is appendicitis, then cranial X-rays can be disregarded as potential laboratory cost drivers.

After an appropriate pool of laboratory cost drivers has been identified, the individual tests are statistically analyzed to quantify the resource usage associated with them. See step 238. Only those tests having a profound impact on resource usage serve as laboratory cost drivers. Process 224 is then concluded at a stopping point 240.

In a preferred embodiment, regression analyses are employed to correlate the usage of the resource of interest with various potential laboratory cost drivers. Any conventional regression analysis may be employed. In one specific embodiment, the SAS/STAT software available from the SAS Institute, Inc. of Cary, N.C. may be employed for this purpose.

After a laboratory cost driver has been identified, it may be validated by various techniques. In one example, validation can be performed by developing and selecting a best explanatory statistical model on 60 percent of records randomly selected from a data set such as that used in step 307 (see FIG. 3A and the associated discussion below). This statistical model will then be applied to the remaining 40 percent of the data sample. Close values for the beta weights in the two models and statistically significant variables in the second model indicate that a valid explanatory model has been identified.

The presence of a laboratory cost driver in a patient's electronic profile does not necessarily mean that the patient had the specified condition used to derive the cost driver. Thus, unlike a match with a selection vector, a match with a laboratory cost driver does indicate that the patient likely had the specified condition. Nevertheless, a match to a cost driver does indicate that statistically, the patient is likely to have deviated from the norm in resource consumption by an amount determined at step 238 of process 224. This is due in part to some association between the test and the underlying condition; a certain fraction of the patients having the test performed have the underlying condition. Various examples of laboratory cost drivers and their associated deviations in resource usage will be set forth below. In general, the laboratory cost drivers find significant value in their ability to predict resource usage.

SELECTION VECTORS AND LABORATORY RESOURCES FOR SEPTIC SHOCK

Septic Shock Selection Vectors

Today, hospitals and other health care organizations are generally reimbursed for a DRG that reflects mainly the principal diagnosis of a patient (the main condition for which the patient was admitted). Many conditions that develops during the course of the patient's stay at the health care organization may not affect reimbursement. Thus, for example, if a diabetic patient is admitted for appendicitis and during her stay at the hospital she develops septic shock, the hospital is reimbursed only for the cost for treating the appendicitis (with an adjustment for her diabetic condition) but not for the costs associated with treating the septic shock. Unfortunately, septic shock arises relatively commonly during the course of a patient's stay at a health care organization. Thus, health care organizations who treat a relatively high percentage of patients developing septic shock may receive relatively low reimbursement for their actual costs and may have difficulty maintaining financial health.

As mentioned above, many hospital discharge records do not directly state that a given patient had a particular condition (septic shock in this case) when, in fact, the patient did have this condition. Identifying those discharge records that do not directly recite septic shock, but which nevertheless represent a patient having septic shock, presents one of the challenges solved by this invention. Most generally, the invention accomplishes this by recognizing that clinically, septic shock arises when one or more bodily systems fail as a result of the toxins produced by an infection. Importantly, that infection must reside in a bodily system or locality that does not form part of the one or more systems that shut down, in order for predictions to be valid. For example, a severe kidney infection may produce enough toxin to poison the respiratory and cardiovascular systems, causing them to shut down. If information in a hospital discharge record reflects this, an appropriately constructed septic shock vector will select that record even though the record does not recite the patient condition code for septic shock.

With this in mind, some preferred selection vectors of this invention include patient condition codes for an infection and one or more organ or organ system failures. The exact patient condition codes employed in such vectors will depend the type of illness under study and the coding system used. Selection vectors for records using ICD-9 codes will contain ICD-9 codes for infections and organ system failures. Selection vectors to be applied to records using ICD-10 codes will contain appropriate ICD-10 codes. If an ICD-9 vector generically covers renal failure, it preferably includes most or all of the different ICD-9 codes specifying a renal failure (e.g., code 586.x for acute renal failure, code 997.5 for post operative renal failure, code 593.9 for toxemia, etc.).

The following is a list of selection vectors which have been identified and proven to accurately identify those patients who contracted septic shock. As explained above, such selection vectors as applied to a collection of electronic discharge records select only those records of patients having septic shock.

Specific Selection Vectors:

1) Septic shock or toxic shock;

2) Sepsis and organ system failure (central nervous system, heart, coagulation, renal, liver, or lung);

3) Infection and organ system failure (central nervous system, heart, coagulation, renal, liver or lung);

4) Lung infection and other organ failure (central nervous system, heart, coagulation, renal, or liver);

5) Kidney infection and other organ failure (central nervous system, heart, coagulation, liver, or lung);

6) Bacteria and electrolyte imbalance and other organ failure (heart, coagulation, liver, or central nervous system);

7) Bacteria and dysrhythmia and other organ failure (renal, liver, coagulation, central nervous system, or lung);

8) Bacteria and fluid imbalance and other organ failure (central nervous system, coagulation, liver, or lung);

9) Fever of unknown origin and two organ systems failure.

Note that the above list ranks the vectors based upon their ability to accurately identify septic shock. This ability was determined by comparison against clinical records (each associated with a corresponding electronic discharge record) which unambiguously confirmed the presence or absence of septic shock. Not surprisingly, the first and second vectors specifically recite septic shock, toxic shock, or sepsis. Thus, some electronic records do accurately record these clinical conditions. However, many other records fail to so record this condition. It is these seemingly incomplete records that pose a problem which the present invention addresses.

The above-listed selection vectors include components comprising generic patient conditions. As noted, there are many different formats for representing these generic patient conditions. In one specific example, the conditions are represented as strings of ICD-9 codes. The following is a list of ICD-9 codes which code for the generic conditions recited in the above selection vectors.

| ICD-9 Codes for Septic Shock | | |
|---|---|---|
| Shock Codes | | |
| Septic shock | 785.59 | |
| Pulmonary shock | 518.5 | |
| Renal Failure | | |
| Acute | 586.x | |
| Post OP | 997.5 | |
| Post trauma | 958.5 | |
| Post labor | 669.3 | |
| Toxemia | 593.9 | |
| Post abortion | 634.3 | through639.3(onlycodesendingon.3) |
| Pulmonary Failure | | |
| ARDS | 518.82 | |
| Resp. failure | 518.18 | |
| On Respirator | v46.1 | |
| Heart Failure | | |
| Fail. w/congestion | 428.0 | |
| Left ventricle fail. | 428.1 | |
| Acute sudden fail. | 428.9 | |
| Cardio-resp. fail. | 799.1 | |
| Circulatory fail. | 799.8 | |
| Septic myocarditis | 422.92 | |
| Toxic myocarditis | 422.93 | |
| Acute hf & renal fail. | 404.93 | |
| Acute vent. fail. | 391.8 | |
| Coagulation Failure | | |
| D.I.C. | 286.6 | |
| Liver Failure | | |
| Hepatic fail. | 572.8 | |
| CNS Failure | | |
| Cerebrovascular collapse | 437.8 | |
| Infections | | |
| Septicemia | 038.xx | |
| Bacteremia | 790.7 | |
| Enterobacteremia | 038.49 | |
| Infect. due to device | 996.62 | |
| Bacterial Conditions | | |
| Specific bacterias | 001.x–005.x | |
| | 008.x–009.x | |
| | 020.x–041.x | |
| | 097.x–098.x | |
| | 100.x–104.x | |

Note that ".x" represents any possible number for this digit.

A complete list of ICD-9 codes for the above-listed selection vectors components—for a specific embodiment—is provided in the Appendix.

Of course, other formats which adequately describe the various patient condition codes may be employed. Among these are ICD-8 codes, ICD-10 codes, CPT-4 codes, ICCS codes, and country-specific codes used in some European data bases.

A knowledge of sepsis pathology may suggest additional patient conditions for use in selection vectors. Among these are treatments with specific antibiotics, monoclonal antibody preparations, and tumor necrosis factors, lactate test use, and use of procalcitonin testing.

The patient conditions provided in the above-identified selection vectors were chosen by a statistically rigorous analysis of a large collection of electronic discharge records and associated clinical data. The selection vectors were found to do a remarkably good job of selecting records representing patients who, on average, consumed nearly identical amounts hospital resources.

Figure 3A:
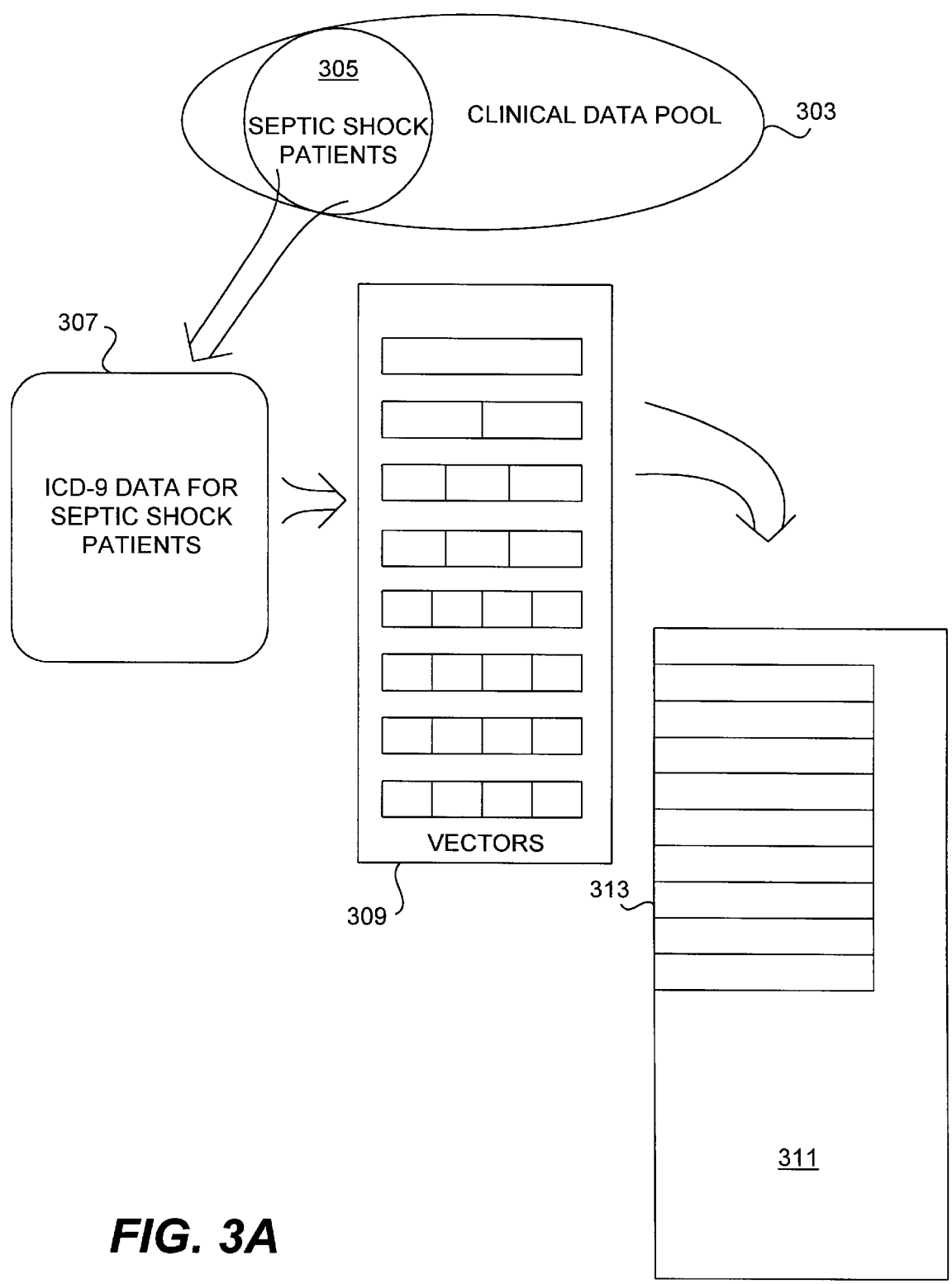
FIG. 3A is a block diagram illustrating how septic shock selection vectors were generated in one example.

Referring now to FIG. 3A, the technique employed to identify the above selection vectors is depicted. This technique represents a specific example of the procedure generally depicted in FIG. 2A. As shown in FIG. 3A, a pool of clinical data records 303 is employed. From these records, a subset 305 containing records for only those patients unambiguously contracting septic shock is identified. In this particular example, records subset 305 contains the clinical data for about 400 patients contracting septic shock. Of course, other statistically significant samples could be derived from other sources, so long as it is clear that each of the patients had septic shock. For each of those patients contracting septic shock, associated electronic discharge records 307 are analyzed.

Thirty to forty DRGs are represented within records group 305. Of these, DRGs 148, 415, 416 (sepsis), 475, and 483 represented nearly fifty percent of the records. See the "DRG Guide," 1997 Ed., Medicode, Inc. Salt Lake City, Utah 1996.

From ICD-9 codes present in the discharge records of group 309, at least tens of thousands of code combinations are possible. From these combinations, nine combinations were identified which comprise specific septic shock selection vectors of this invention. These combinations were identified by first ranking by frequency all ICD-9 codes appearing in the discharge records 307. The inventor then applied her judgment and knowledge of sepsis and septic shock pathology to identify those combinations that likely specified septic shock implicitly. Of course, other techniques for generating the selection vectors—such as those generation techniques described above—could have been employed. In the end, the selection vectors in group 309 included between one and four ICD-9 codes.

As shown, a collection of selection vectors 309 is thereby generated. Together, all nine selection vectors account for 100 percent of the septic shock cases identified from clinical data set 305 and which contained a minimum of three ICD-9 codes, at least one of which was a procedure code. (This last condition is a minimum criteria for meaningful data.) As indicated above, the first vector simply recites the patient condition code for septic shock or toxic shock (ICD-9 code 785.59 in this example). Discharge records having this correct coding accounted for only about 27 percent of the total records for patients known to have septic shock (i.e., 27 percent of the total records in discharge records group 307). Other vectors were necessary to identify the remaining records from within group 307. Generally, these vectors include (1) an infection, possibly of unspecified origin and (2) a system shut down (e.g., renal or heart shut down). In this example, the remaining eight selection vectors identified above capture the remaining 73% of the septic shock cases. In essence, the selection vectors other than the first one directly reciting the septic shock patient condition code contain codes that implicitly identify septic shock in a language other than the expected direct language.

The selection vectors were validated by applying them to a very large data set of discharge records 311 which included records for both patients with and without septic shock (e.g. patients admitted for heart disease, abortions, and other condition unrelated to sepsis). In fact, data set 311 included 27 percent of all hospital admissions in the US for the year 1995 (corresponding to millions of hospital admissions). From this large data set, 1000 discharge records were selected for each month of 1995. These 12 sets of 1000 records each (subset 313) were selected by matching the selection vectors within group 309 to the records of data set 311. Thus, it was believed that the records within subset 313 were limited to records for patients that had septic shock.

For each of the twelve monthly groups of subset 313, the mean cost of patient treatment and the death rate were extracted. The variation in cost was from about $100 to about $948,000 (corresponding to six standard deviations). Quite surprisingly, it was found that the mean treatment costs of the twelve monthly groups within subset 313 were within about $3,500 of one another. The institutional death rate for septic shock normally varies between about 9 percent and 26 percent. Also surprisingly, it was found that the death rates between the twelve monthly groups of record subset 313 varied within 8 percent. This establishes that the septic shock selection vectors developed as described above correctly select patients of similar cost (resource consumption). More generally, it confirms that the septic shock selection vectors were able to identify patients having quite similar conditions.

Within each of the twelve monthly groups, there were quite large variations in outcome (death rate) and cost (between about $100 and $1,000,000). This variation may be due to different efficiencies of the various hospitals in the US, etc. However, in a large enough mix of US hospitals, the selection vectors of this invention identify septic shock patients having, on average, similar outcomes and similar charges.

While the above-listed septic shock selection vectors all identify records for patients who had septic shock, they vary in the types of septic shock that they identify. Septic shock comes in varying degrees of severity, often based upon the difficulty of treating septic shock with antibiotics. For example, sepsis in the kidneys or urinary system is often relatively easy to treat (and hence less severe), while sepsis in the bones, extremities, or closed organs is much more difficult to treat. The various selection vectors identified above may select predominately or exclusively records for patients having a specific type of septic shock (e.g., septic shock associated with an infection of the kidneys). Not surprisingly, the costs of treating septic shock may vary dramatically depending upon the origin of that septic shock. For example, treating septic shock originating with an infection of the kidneys or urinary system costs significantly less, on average, than treating septic shock originating with a bone infection. This results because antibiotic treatment cures urinary system infections much faster, on average, than it cures bone infections. Hence septic shock associated with a urinary system infection can generally be treated less expensively than septic shock associated with a bone infection.

As a result, the selection vectors that select one type of septic shock over another type also correspond to different treatment costs. It was found during the validation procedure that the first selection vector (containing patient condition codes for septic shock or toxic shock) was associated with an increase in treatment costs of about $2000 on average over the cost of care for sepsis. The remaining eight septic shock selection vectors all similarly predicted a large increase in treatment costs over the cost for simple sepsis.

Health care organizations can generally benefit from identifying which types of septic shock its patients have or had. This allows them to adjust risk based upon the types of patients that they typically handle. It also allows the health care organization to intelligently design and implement guidelines for treating septic shock. For example, a hospital may determine that for those patients appearing to have sepsis of the urinary tract, a relatively limited treatment regime can be employed. Appropriate guidelines to this effect could then be monitored using the selection vectors of this invention. That is, by applying a selection vector identifying urinary tract sepsis to the electronic discharge records of a hospital implementing these guidelines, one identifies only those patients having urinary tract sepsis. Patients treated according to the guidelines and identified by the urinary system selection vector should have a relatively low treatment cost under the guidelines. If not, one may assume that the guidelines are not being followed.

More generally, the information provided with the selection vectors of this invention provides some insight into which classes of patients are likely to develop sepsis or have actually had septic shock. Such information can be used by the health care organization to evaluate its financial performance. This information may also be used for risk adjustment, whereby health care organizations accepting riskier patients are reimbursed for taking that risk.

Figure 3B:
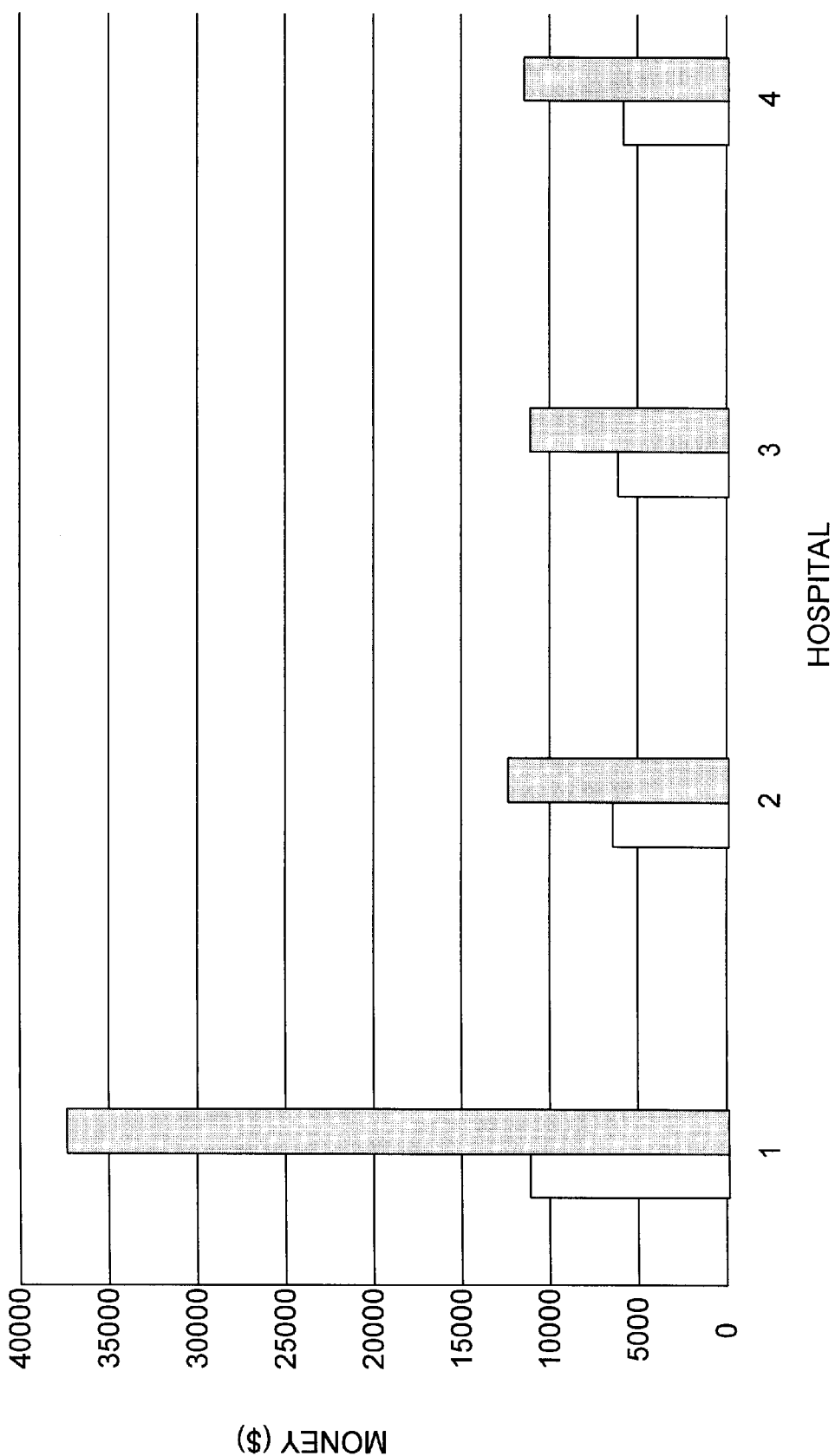
FIG. 3B is a graph ranking four hospitals in their costs of treating similarly severe septic shock patients.
Figure 3C:
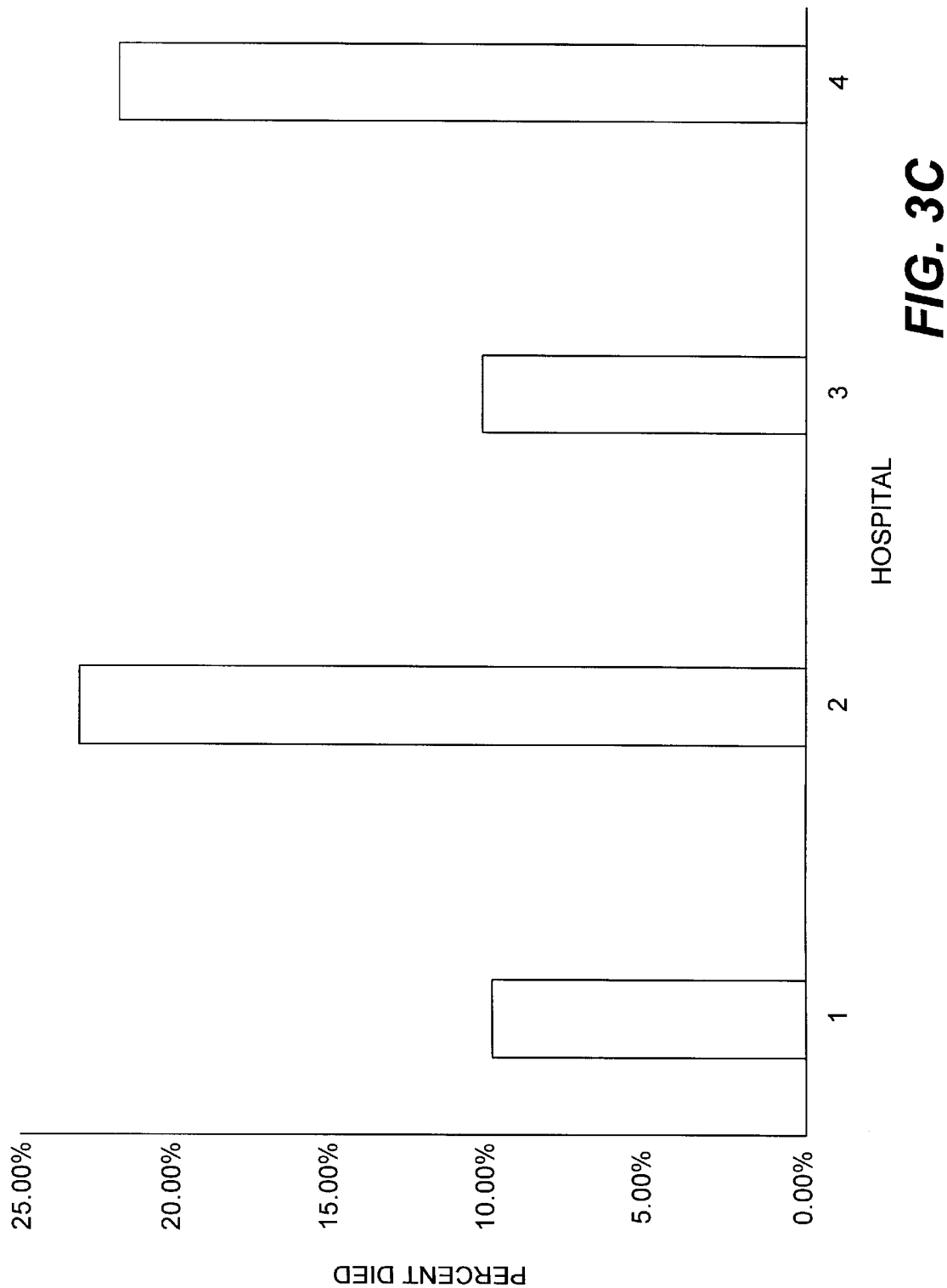
FIG. 3C is a graph ranking the four hospitals of FIG. 3B in terms of their treatment outcomes (death rates specifically) in treating similarly severe septic shock patients.

FIGS. 3B and 3C illustrate one example of how the selection vectors of this invention have been applied to compare competing hospitals. Initially, the electronic discharge records were compared against the above selection vectors to identify a class of similarly severe septic shock patients in each hospital. Prior to this invention, such filtering to identify similar classes of patients across hospitals was either impossible or too laborious to execute.

FIG. 3B illustrates the Medicare payment (left bar) and average actual charges incurred (right bar) for the selected class of septic shock patients for each of hospitals 1, 2, 3, and 4. As can be seen, hospital 1 had actual costs far outstripping those of the other three hospitals. Thus, armed with this information, a HMO or other contractor might be disinclined to contract with hospital 1. Similarly, hospital 1 might decide reassess its treatment procedures for sepsis/septic shock patients.

FIG. 3C illustrates the adjusted death rates (adjusted to have similar distribution of risk) for the selected class of septic shock patients for each of the hospitals 1, 2, 3, and 4. As can be seen, hospitals 2 and 4 had death rates far in excess of hospitals 1 and 3. Armed with this information, a patient or a provider organization would likely select hospitals 1 and 3 over hospitals 2 and 4. Hospitals 2 and 4 might reassess their procedures for treating sepsis/septic shock patients. In light of the cost data in FIG. 3B and the outcome data in FIG. 3C, hospital 3 appears to have the best procedures for treating the selected class of septic shock patients.

Sepsis Laboratory Cost Drivers (Laboratory Tests)

While the septic shock selection vectors discussed above do a good job of identifying from hospital discharge records those patients having septic shock, they only partially explain the resources consumed by any given sepsis of septic shock patient. It has been found that when the septic shock selection vectors are used in conjunction with laboratory cost drivers associated with sepsis therapy, a remarkably good prediction of total resource usage is obtained. These tests likely predict just how severe was the patient's sepsis of septic shock.

| | |
|---|---|
| Gram Stain | $730 |
| Transfusion Cross-Match | $482 |
| Chemistry Panel 12 | $261 |
| Unspecified Lab Test | $535 |
| Urinary Microscopy | −$564 |
| Unspecified Bacteria Test | $189 |
| Serum Magnesium | $463 |
| Bacterial Sensitivity | $218 |
| Random Glucose | $92 |
| A.P.P.T.* | $516 |
| MIC** | $426 |
| Blood Gases | $603 |
| Leukocyte Differential | $375 |
| Chemistry Panel 7 | $658 |

-continued

| | |
|---|---|
| Specimen Collection | $102 |
| Aerobic or Anaerobic Bacterial Culture | $995 |
| Aerobic Culture | $498 |
| Complete Blood Count (CBC) | $1,002 |

*Activated Partial Protrombintine
**Minimize Inhibitory Concentration

Generally, the above tests should be well known to those of skill in the art. For example, the transfusion cross-match test determines whether blood types are compatible for a transfusion. A patient having this laboratory cost driver has been thought to need or has received a transfusion. Thus, if the patient had sepsis, it was at least a moderately severe case of sepsis and the cost of treatment went up accordingly (by $482 per cross-match on average). The chemistry profile is a sodium, potassium, chloride electrolyte concentration profile. Urinary microscopy refers to a microscopic examination of a urine sample. Interestingly, for each additional urinary microscopy performed, the charges of an admission actually falls, on average, by $564. As mentioned, urinary infections are often easier to treat (and generally cheaper). Each serum magnesium test indicates that the treatment cost will go up by an additional $463. Such tests suggest that the patient was going into electrolyte imbalance. The bacterial sensitivity test determines whether the bacteria infecting the patient is sensitive to prescribed antibiotics. The A.P.P.T. test tests for coagulation. The blood gases test tests for $CO_2$ and $O_2$ in the blood. The leukocyte differential test measures the difference in abundance between lymphocytes and granulocytes. The specimen collection covers generic specimens (e.g., wound, blood, urine, etc.). The complete blood count and anaerobic and aerobic bacterial cultures have the biggest impact on cost.

Figure 4:
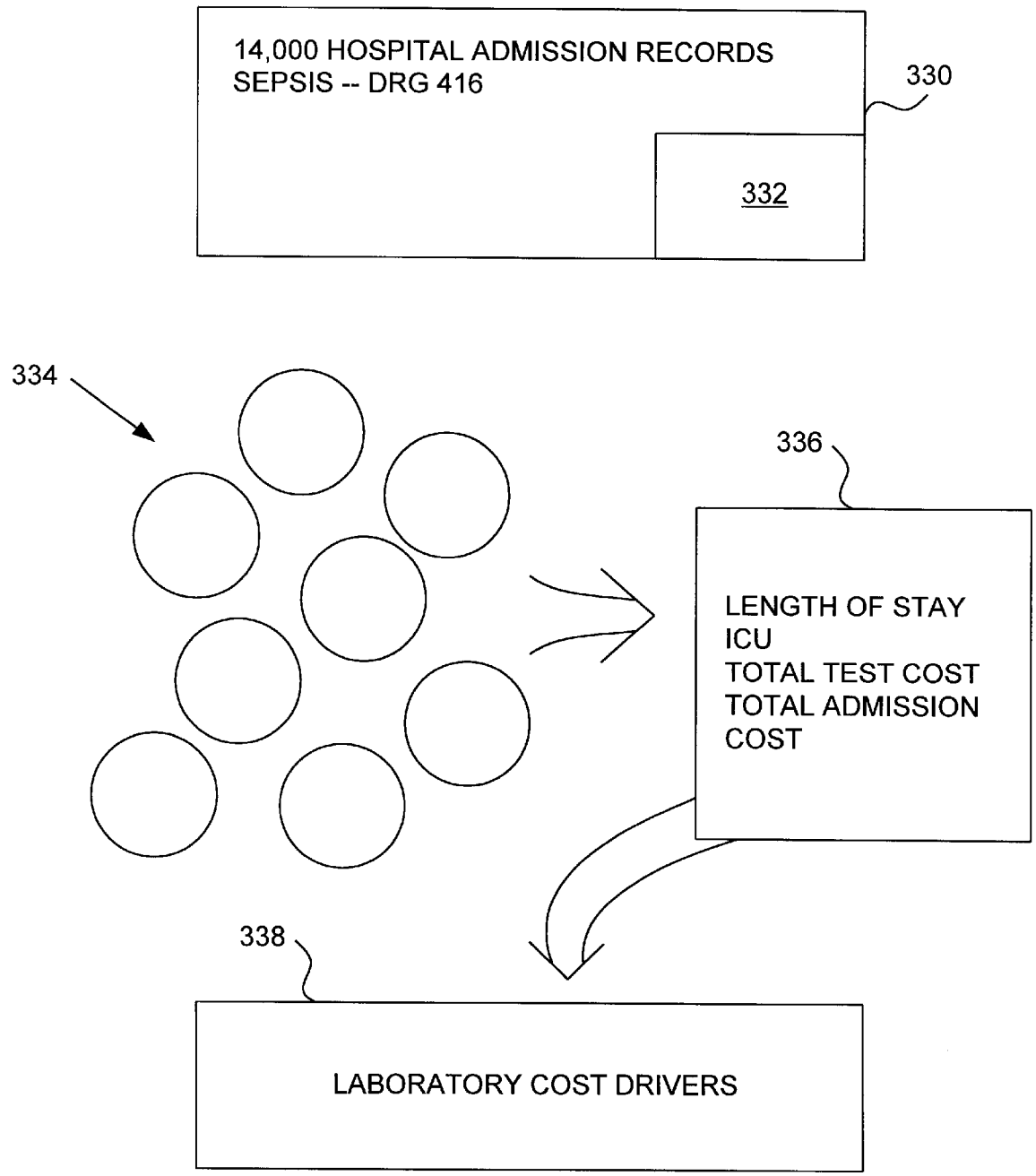
FIG. 4 is a block diagram illustrating how laboratory cost drivers were generated in one example.

FIG. 4 graphically depicts the process by which the laboratory cost drivers presented above were derived. This serves as a specific example of the process generally depicted in FIG. 2B. Initially, a data set 330 for about 14,000 admissions for patients having sepsis was obtained. All sepsis admissions were identified by virtue of falling within the sepsis DRG classification (DRG 416). As explained above, many patients who have been treated for septic shock are never actually classified in DRG 416 because their electronic discharge records either do not recite the ICD-9 code for septic shock or sepsis, or recite it in a field other than the principal diagnosis code field. Of course, those patients classified in the sepsis DRG will assuredly have had sepsis during their treatment. Thus, the patient records considered in this study definitely describe patients who had sepsis. Of course, the septic shock vectors described above could have also been used to accurately identify records of septic shock patients not classified into DRG416.

In this instance, data set 330 included a set of ICCS codes 332 which detailed the laboratory tests employed on the sepsis patients, however, other sources of laboratory test usage may also be suitable for this purpose. The laboratory tests in records 332 were sorted by volume (how often the test was performed in the 14,000 admissions). Then the high volume tests having a logical relation to sepsis were selected. Some high volume tests such as a hemoglobin test are simply unrelated to sepsis and could be disregarded. Those laboratory tests passing through this filter were separated into bins 334 by volume. Then the tests in the bins were analyzed in a comparison block 336 for four categories of resource usage: length of hospital stay, ICU use, total test cost, and total admission cost.

Next, a multivariate regression analysis was performed to identify a correlation between tests performed (laboratory cost drivers) and resource usage. In this analysis, the charges for a patient are analyzed as a function of combinations of laboratory cost drivers and sometimes selection vectors. Hundreds of regressions were performed on various laboratory test data with a statistical analysis routine (SAS/STAT Software available from the SAS Institute, Inc. of Cary, N.C.). The combinations of tests that best predicted total charges for patient treatment were selected as laboratory cost drivers 338 for a resource usage model. The expression resulting from this analysis has been found to explain 85 to 91 percent of the variation in charges for an individual hospital's charges for patients falling within DRG 416 (sepsis). For comparison, known risk adjustment tools can explain no more than about 42 percent of the variance in charges in such a DRG population.

Expressions for Modeling Health Care Resource Usage

From the above septic shock selection vectors and sepsis laboratory cost drivers, expressions were derived for modeling resource usage for a patient as a function of these vectors and cost drivers. In their simplest forms, these expressions express the total cost of a health care admission as linear functions of the above laboratory cost drivers, assorted well-known generic cost drivers, and any one of the above selection vectors. Such expressions have multiple terms each comprised of a coefficient (parameter) and one of these variables (vector, cost driver, etc.).

If the variable is a laboratory cost driver, the value of its term in the expression is the product of its coefficient and the number of times that laboratory test was performed during treatment. Thus, if a laboratory test represented in the expression was not performed during the patient's treatment, then the term does not contribute to the cost of treatment. If the test was performed once, one times the associated coefficient is summed with other terms of the expression. If the test was performed twice, two times the associated coefficient is summed with other terms of the expression, and if the test was performed "n" times, n times the coefficient is summed.

If the variable is a selection vector or a generic binary cost driver, the value of the associated term is (i) zero if the vector or binary cost driver fails to match the patient's electronic profile and (ii) the value of the coefficient itself if the vector or binary cost driver does match the electronic profile. No higher multiples of such coefficient are possible.

FIGS. 5A and 5B present a list of the terms in an expression developed as described above. The values of the various terms are summed. The following variables may be either zero or one: selection vector ("PRIME VECTOR"), SPEC. UNIT, SURGERY, DIED, BEDS 199, BEDS 299, BEDS 500, NORTHEAST, and NORTH-CENTRAL. In this expression the selection vector is the first septic shock vector identified above (i.e., the vector specifying the patient condition codes for septic shock or toxic shock). If this vector matches the patient's electronic profile, then variable value is one. If not, then variable value is zero. When patient was treated in an intensive care unit or a critical care unit, then the SPEC. UNIT variable equals one. When a surgical procedure was performed on the patient, the SURGERY variable equals one. When the patient dies during treatment, the DIED variable equals one. When patient receives treatment in hospital having between 0–199 beds, the BEDS 199 variable equals one. When patient receives treatment in hospital having between 200–299 beds, the BEDS 299 variable equals one. When patient receives treatment in hospital having more than 500 beds, the BEDS 500 variable equals one. When the patient receives treatment in the Northeastern part of the US (i.e., the New England states, New York, New Jersey, and Pennsylvania) the NORTH-EAST variable equals one. And when the patient receives treatment in the North Central part of the US (i.e., Illinois, Indiana, Iowa, Kansas, Michigan, Minnesota, Missouri, Nebraska, North Dakota, Ohio, South Dakota and Wisconsin), the NORTH-CENTRAL variable equals one.

All other variables are laboratory cost drivers and may have any integer value. More specifically, the value of each laboratory cost driver variable is an interger equaling the number of times that the associated laboratory test was performed. The "INTERCEPT" term in the expression is the "y axis" intercept, assuming that the expression takes the form y=INTERCEPT+Σ(PARAMETER*VARIABLE). In this expression, the intercept value is –$10.22.

The coefficients have units of US dollars. Thus, if the selection vector is present in a record, $1955 will be subtracted from the cost of treating the patient. If the hospital is located in the Northeastern part of the country, the associated term of the expression contributes $3406.37 to the cost of treating the patient. In the case of a complete blood count laboratory test performed once, the average cost of treating a patient increases by $1001.97. When the complete blood count test is performed twice, the average cost jumps by $2003.94, and so on.

Other forms of the above expression may be employed. For example, other selection vectors may be substituted. When this occurs, the coefficients of the selection vector and other expression variables (including the laboratory cost drivers) change as does the value of the function's intercept. However, for the nine above-listed septic shock selection vectors, the form of the above expression is identical and the parameter values vary only slightly. This above expression (as developed for each of the above-presented nine septic shock selection vectors) explains at least about 85 percent of the variance in patient charges found in the conventional DRG 416 patient categorization.

The following expressions calculate the charges for treating an average sepsis patient (not having septic shock) and an average patient having septic shock. These were derived by a method similar to that employed to derive the above cost expression for septic shock patients. However, they were normalized for geographic location and hospital size. Thus, the associated parameters do not appear in the expressions.

|  | Vector 1 Septic Shock | Low Risk Sepsis |
| --- | --- | --- |
| Intercept | $5615 | $2681 |
| ICU | 2977 | 2950 |
| Surgery | 3595 | 2754 |
| Died | −4301 | −1963 |
| Amylase | 690 | 216 |
| Blood gases | 576 | 846 |
| CBC | 998 | 445 |
| Chem. 20 | 716 | 619 |
| Creatin. Kinase | −1425 | 72 |
| Coagulation | −45 | 230 |
| Creatinine | −596 | −107 |
| Culture | −17 | 511 |
| Glucose | 246 | 91 |
| Gram Stain | 2071 | −498 |
| Electrolytes | 765 | 880 |
| Magnesium | 262 | 661 |
| Specimen col. | 137 | 99 |
| Urine | −1664 | −190 |

-continued

|  | Vector 1 Septic Shock | Low Risk Sepsis |
| --- | --- | --- |
| Cross Match | 40 | 848 |
| R square | 0.73 | 0.52 |
| Adj. R. square | 0.72 | 0.52 |
| Death Rate | 50.9% | 7.7% |

The "Vector 1" expression applied to only those patients having electronic discharge records matching the first septic shock selector vector listed above (i.e., records having an ICD-9 code for septic shock or toxic shock). The "Low Risk" expression applies to only those patients having sepsis but not septic shock.

Upon inspection of these expressions, it can be seen that hospitals incur significantly less costs in treating an average sepsis patient than in treating an average septic shock patient. This is evidenced primarily by the more than 100 percent increase (nearly $3000) in the intercept of the septic shock expression over the sepsis expression. Nevertheless both patient categories fall under DRG 416, and therefore hospitals receive the same reimbursement from Medicare for these patients. Obviously, the ability to segregate septic shock patients from sepsis patients generally allows an important risk adjustment.

APPLICATIONS EMPLOYING VECTORS AND LABORATORY RESOURCES

In general, the systems of this invention select patients having certain electronic profiles which match a selection vector. The systems accomplish this by determining whether a patient has the collection of patient condition codes found in the selection vector being considered. Each and every one of the codes in the vector must be present in the patient's electronic profile in order for the record to match the vector. A match between the vector and the electronic profile confirms that the patient has the condition (or condition severity) specified by the vector. Laboratory cost drivers may also be employed to aid in the selection process.

After the patients have been classified by the selection vector(s) and laboratory cost driver(s), if necessary, their actual outcomes and/or costs may be determined and compared against similar patients treated at other health care organizations as described above with reference to FIGS. 3B and 3C. In addition, or alternatively, the system may calculate an adjusted cost and/or adjusted outcome for treating the classified patients. This may be accomplished with an expression such as that illustrated in FIGS. 5A and 5B.

Figure 6A:
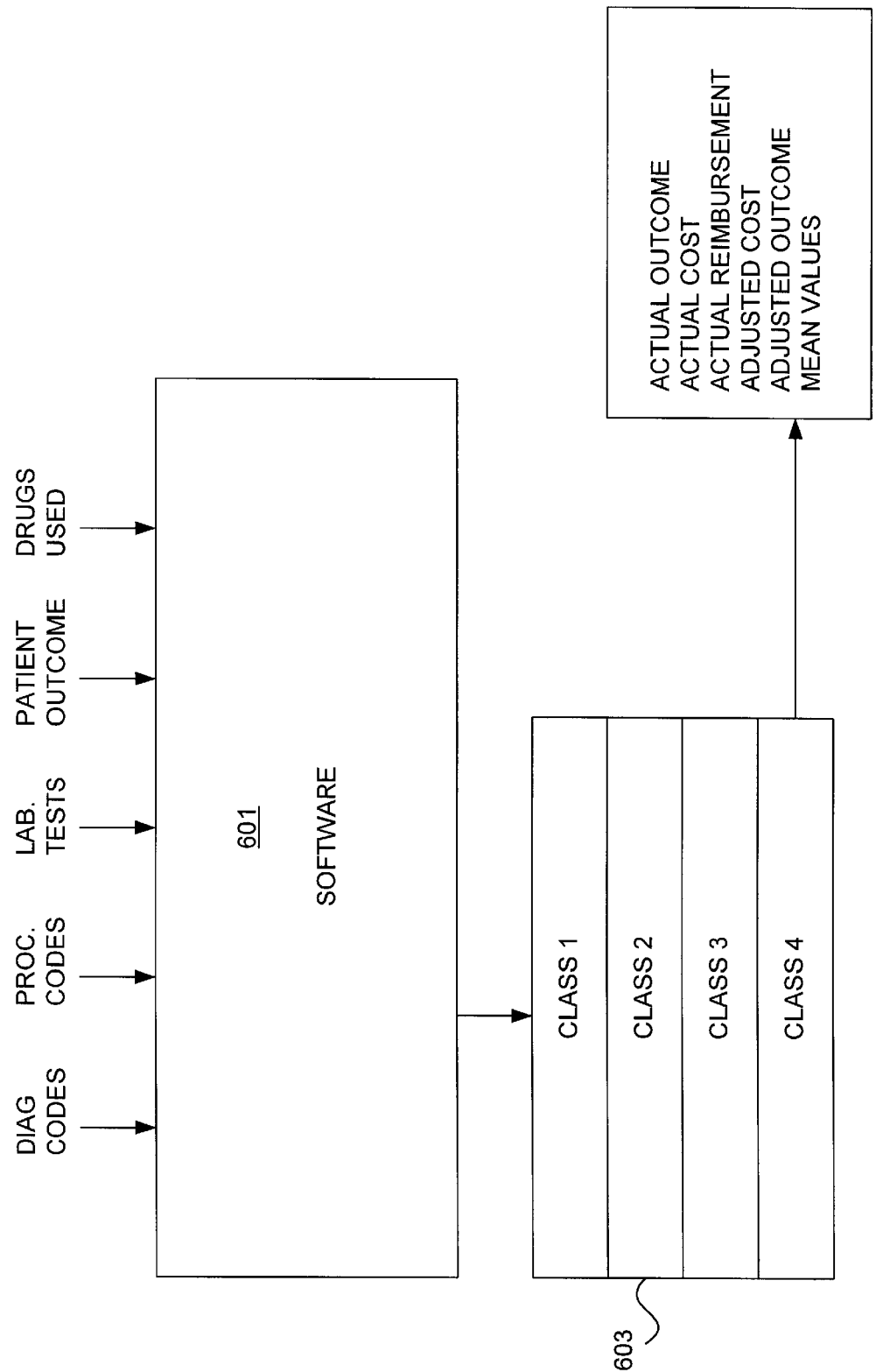
FIG. 6A is a block diagram illustrating the inputs and outputs of a software program for analyzing health care organizations in accordance with a preferred embodiment of this invention.

FIG. 6A illustrates some typical inputs and outputs of software implementing the methods/systems of this invention. The illustrated software 601 may run on any suitable computing device such as those described above and illustrated generically in FIG. 1A and stored on any suitable computer readable medium. As shown, software 601 may accept as inputs (a) diagnostic codes (e.g., items 158 and 160 in the FIG. 1B form), (b) procedure codes (e.g., items 162 and 164 in FIG. 1B), (c) laboratory tests performed, (d) patient outcome data (e.g., death or survival), and (e) drugs used in the treatment. Software 601 may also output various classes of patients 603 based upon medical condition and/or severity the medical condition. For any combination of these classes, software 601 may also output the following information, for example: (a) actual patient outcome, (b) actual treatment cost, (c) actual reimbursement for the treatment, (d) predicted cost adjusted for patient classification, (e) predicted patient outcome adjusted for patient classification, and (f) mean values of any of the foregoing for other comparable health care organizations.

Figure 6B:
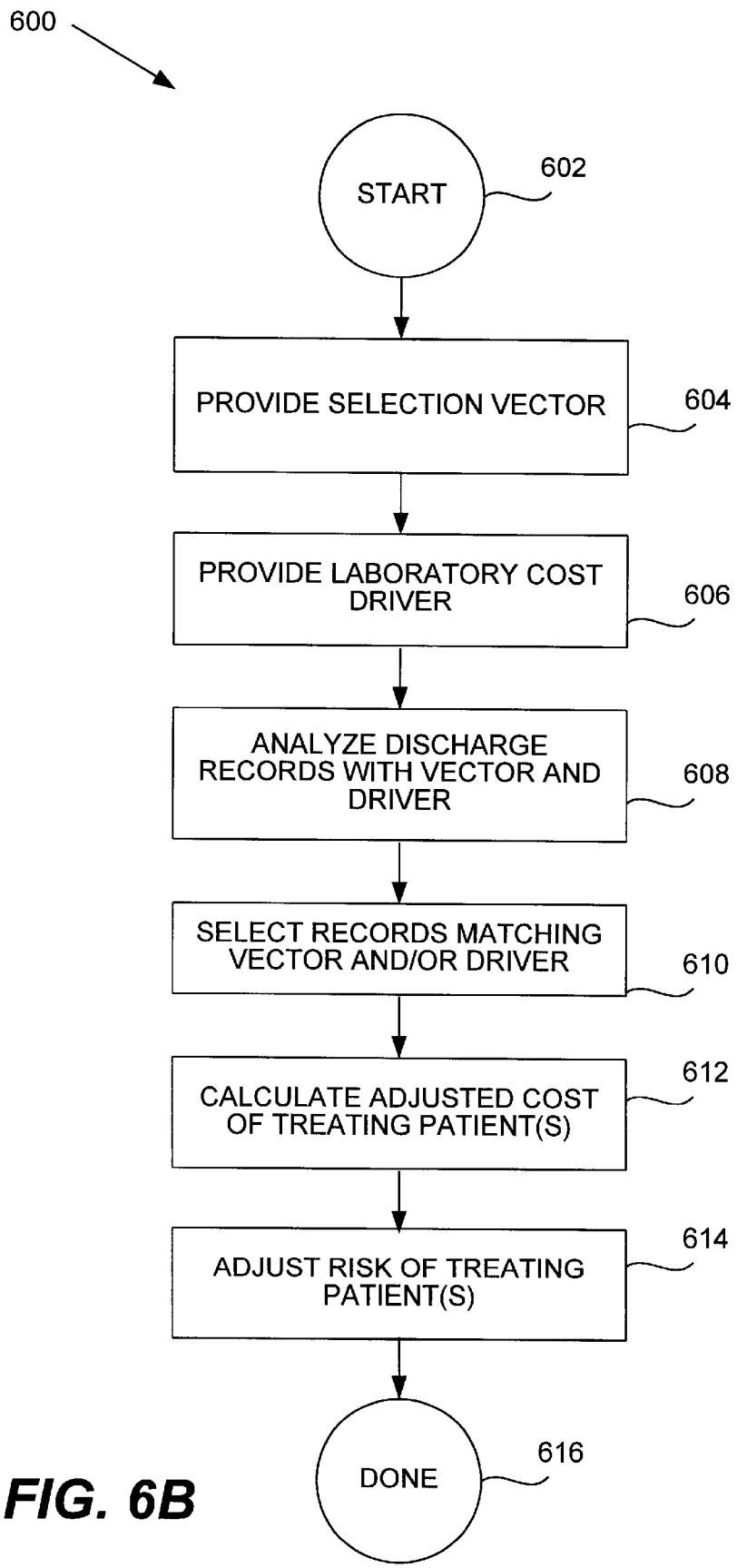
FIG. 6B is a process flow diagram of a method for analyzing health care organizations in accordance with a preferred embodiment of this invention.

FIG. 6B is a process flow diagram depicting various of the procedures 600 that might be employed by software 601 or other suitable computer program product. Process 600 begins at a starting point 602 and from there the system provides (1) an appropriate selection vector for a specified condition of interest (step 604) and (2) an appropriate laboratory cost driver (or drivers) for the specified condition (step 606). Then at a step 608, the system analyzes a specified set of electronic patient profiles with the selection vector and laboratory cost driver(s). This may be accomplished by matching the cost drivers and vector components against the data contained in the electronic patient profiles—although other analysis criteria may be employed. From there, the system selects patient profiles (at a step 610) that match the analysis criteria of step 608. The selected patient profiles should all have the specified medical condition. Thereafter, the system may optionally calculate an adjusted cost of treating the patients at a step 612. At this point, the system may also group the selected patients according to severity, cost, outcome, or other appropriate characteristic. Finally, the system may optionally perform a risk adjustment, at a step 614, based upon the classification or grouping of patients. Process is complete at 616.

The systems of this invention and their outputs may be employed by a health care organization to explain why its costs are higher or lower than the norm. If a health care organization treats sicker than normal patients, the models of this invention can prove this thereby allowing the hospital to justify its costs to an HMO or other entity with whom it would like to do business.

In addition, this invention can suggest how a health care organization should perform if it implements a particular guideline for a particular class of patients. Such guidelines may cover how an organization tests the patients, the kinds of drugs administered to the patients, when a patient is admitted to an intensive care unit, how early in the treatment patients are tested for drug susceptibility, how many of these tests are run a particular patient. In one example, guidelines for patients having severe cases of sepsis may specify that the patients are tested for drug susceptibility relatively early in the process. In this manner, the care provider can provide the correct drug earlier in the treatment process.

One can use the methods of this invention to determine whether patients successfully treated under a proposed or temporary guideline are representative a large class of patients or are special cases. For example, a guideline for sepsis treatment might specify that patients suspected of having sepsis are immediately given a series of five specific tests. If the outcomes of tests A, B, and D are positive, then the patient is transferred to the intensive care unit. Now if it is found that the patients treated under this guideline have successful outcomes (they cost less and recover more often without complications), the models of this invention may show that these patients were merely a special case (e.g., the less severe cases of sepsis or cases that are easily treated such as urinary system infections) or were part of a larger class (e.g., all suspected sepsis patients).

A health care organization will want to know how many of the patients successfully treated under its guidelines are actually representative of what the organization would normally see in a given time period. In other words, the organization wants to know how many of these patients it could successfully manage under the guidelines. If the number is large, then the guideline could be broadly applied. If the number is small and limited to a marginal group of patients, then the guideline should be applied to an appropriate smaller group of patients.

Without applying the methods of this invention, the health care organization might conclude that its new guideline could be applied to all sepsis patients. If in fact only thirty percent of the patients are of a severity that can be effectively managed according to that guideline, then the health care organization is in for an unpleasant surprise when it broadly implements the guideline.

In a simple example, the patients treated under the guidelines could be classified by applying multiple vectors to the patient discharge records. If the vector (or collection of vectors) that matches covers a wide range of patient classes, then it can be assumed that the guidelines should be applied across all classes. If more limited vectors match the treated patients, then the guidelines should be applied more narrowly.

RANGE OF EMBODIMENTS

Although the foregoing invention has been described in some detail for purposes of clarity of understanding, it will be apparent that certain changes and modifications may be practiced within the scope of the appended claims. Furthermore, it should be noted that there are alternative ways of implementing both the process and apparatus of the present invention. Accordingly, the present embodiments are to be considered as illustrative and not restrictive, and the invention is not to be limited to the details given herein, but may be modified within the scope and equivalents of the appended claims.

APPENDIX

| CONDITIONS | ICD9 CODES INCLUDED | CODE EXPLANATION |
| --- | --- | --- |
| Septicemia | 003.1 | Salmonella septicemia |
| | 038.xx | Septicemia |
| | 639.0 | Septicemia due to childbirth |
| | 999.3 | Septicemia due to infusion |
| Bacterial infection | 031.8 | B. Bronchisepticia |
| | 033.1 | Bordatella parapertussis |
| | 036.0 | Meningococcus |
| | 040.xx | Other bacterial diseases |
| | 041.xx | Bacterial infections in conditions classified elsewhere and of unspecified site |
| | 998.5 | Post op infection |
| | Procedure code 99.21 | Infusion of antibodies |
| Site-specified infections, except lungs or kidneys | 042.1 | HIV causing other specific infections |
| | 320.xx | Bacterial meningitis |
| | 322.xx | Unspecified meningitis |
| | 440.24 | Athrosclerosis with gangrene |
| | 540.x | Acute appendicitis |
| | 567.0 and 567.2 | Peritonitis, infectious |
| | 577.0 | Acute pancreatitis |
| | 996.6x | Infection or inflammation due to implant |
| | 998.5 | Post op. infection |
| Kidney infection | 590.xx | Infection of kidney |
| | 595.0 | Acute cystitis |
| | 599.0 | Bacteriuria |
| Lung Infections | 481.xx | Pneumococcal pneumonia |
| | 482.xx | Other bacterial pneumonia |
| | 484.3 | Pneumonia in whooping cough |
| | 507.0 | Pneumonia due to inhalation of food or vomitus |
| | 513.0 | Lung abscess |

-continued

| CONDITIONS | ICD9 CODES | CODE EXPLANATION |
|---|---|---|
| Fever | 780.6 | Fever of unknown origin |
| Disorders of electrolytes | 276.2 | Acidosis |
|  | 276.3 | Alkalosis |
|  | 276.4 | Mixed acid-base disorder |
|  | 276.7 | Hyperkalemia |
|  | 276.8 | Hypokalemia |
|  | 276.9 | Not classified |
| Fluid disorders | 276.0 | Hyperosmolality |
|  | 276.5 | Volume depletion |
|  | 276.6 | Fluid overload |
| Dysrythmias | 427.0 | Tachycardia |
|  | 427.1 | V. Tach. |
|  | 427.3x | Atrial fibrillation |
|  | 427.4x | Ventricular fibrillation |
|  | 427.6x | Premature beats |
|  | 427.8x | Other dysrythmias |
|  | 427.9 | Other rhythm disorders |
| Shock | 785.59 | Septic shock |
|  | 998.0 | Post operative shock, endotoxic, hypovolemic, septic |
| Toxic shock | 040.89 | Toxic shock syndrome |
|  | 639.5 | Shock due to sepsis in childbirth |
| Renal failure | 586 | Renal failure unspecified |
|  | 584.xx | Acute renal failure |
|  | 996.73 | Complic. of renal dialysis |
|  | 997.5 | Renal failure, tubular necrosis, anuria due to complications |
|  | 788.5 | Oliguria/anuria |
|  | 403.91 | Hypertension with renal failure |
|  | Procedure code 39.65 | Hemo-dialysis |
|  | Procedure code 39.95 | ECMO |
| Pulmonary failure | 518.5 | Pulmonary insufficiency following trauma and surgery |
|  | 518.81 | Respiratory failure |
|  | 518.82 | ARDS |
|  | 799.1 | Cardio-respiratory failure |
|  | V44.0 | Tracheostomy |
|  | V461 | Respirator |
|  | Procedure code 31.1 | Tracheostomy |
|  | Procedure code 96.7x | Continuous mechanical ventilation |
|  | Procedure code 39.66 | Percenteral cardio-pulm. bypass |
| Hepatic failure | 997.4 | Hepatic failure |
|  | 570.x | Hepatic failure, coma |
|  | 572.2 | Hepatic coma |
|  | Procedure code 50.92 | Hemo-dialysis for hepatic assistance |
| CNS failure | 293.xx | Transient organic psychosis |
|  | 434.xx | Cerebral infarct |
|  | 310.xx | Organic brain syndrome |
|  | 997.0 | Anoxic brain damage |
|  | 996.2 | Mechanical complication of nervous system device |
|  | 780.02 | Transient Alteration of awareness |
| Cardiac failure | 227.5 | Cardiac arrest |
|  | 428.x | Heart failure |
|  | 799.1 | Cardio-respiratory failure |
|  |  | Heart syncope |
|  | 992.1 | Heart syncope with arrest due to complications |
|  | 997.1 |  |
|  | 585.5 | Cardiac shock |
| Coagulophaty | 286.6 | DIC |
|  | 997.2 | Phlebitis or thromboplebitis due to complications |
|  | 286.7 | Acquired coagulation factor deficiency |
|  | 286.9 | Unspec. coag. defect |
|  | 287.5 | Throbocytopenia unspecified |

What is claimed is:

1. In a computer system, a method of classifying patients according to an underlying condition, the method comprising:

providing a selection vector of patient condition codes which specify a selected medical condition without explicitly reciting that selected medical condition;

providing a laboratory cost driver which specifies a laboratory test which may be performed during the course of a patient's treatment;

analyzing a plurality of electronic discharge records of one or more health care organizations to determine which of those electronic discharge records recite patient data which match the (i) patient condition codes of the selection vector and (ii) the laboratory test of the laboratory cost driver; and selecting those electronic discharge records matching at least one of the selection vector and the laboratory cost driver, wherein the selected electronic discharge records represent a class of patients having the selected medical condition, wherein the selection vector has a sensitivity of at least about 80 percent for the selected medical condition and a specificity of at least about 70 percent for the selected medical condition.

2. The method of claim 1, wherein the selected class of patients has an expected deviation from a normal amount of reimbursement.

3. The method of claim 1, wherein the patient condition codes are provided as at least one of ICCS codes, DRG codes, CPT-4 codes, ICD-8 codes, HICS codes, ICD-9 codes, and ICD-10 codes.

4. The method of claim 1, wherein the selection vector has an associated cost parameter which may be used to determine an expected cost for treating a patient having an electronic discharge record matching the selection vector.

5. The method of claim 1, wherein the selected medical condition is septic shock.

6. The method of claim 1, wherein the laboratory cost driver includes an associated cost parameter which may be used to determine an expected cost for treating a patient having an electronic discharge record matching the laboratory cost driver.

7. The method of claim 6, wherein the laboratory cost driver is chosen such that its effect on the cost of treatment is at least about three times the cost of the associated laboratory test.

8. The method of claim 1, further comprising calculating an amount of resources expected to be consumed based upon an expression including as variables a plurality of laboratory cost drivers.

9. The method of claim 8, wherein the variables of the expression further comprise the selection vector.

10. The method of claim 8, wherein the expression is a linear expression.

11. The method of claim 8, wherein the expression is used in risk adjustment to classify patients based upon the amount of resources expected to be consumed.

12. The method of claim 9, wherein the expression is used to confirm that medical treatment guidelines are being followed by a health care organization.

13. A method implemented on one or more computer systems for classifying patients according to risk, the method comprising:

determining whether patient information provided as one or more electronic records matches a selection vector specifying a collection of patient conditions;

determining whether said patient has had one or more tests from a prescribed group of tests performed, and classifying said patient in a specified risk group based upon whether that patient's electronic discharge records match said selection vector and whether that patient's electronic discharge records for tests performed indicates that the patient has had specific ones of said defined tests performed, wherein the selection vector has a sensitivity of at least about 80 percent for a specified medical condition and a specificity of at least about 70 percent for the specified medical condition.

14. The method of claim 13, wherein the specified risk group correlates with an expected cost for treating said patient, which expected cost is derived from a statistical analysis of a group of patients.

15. The method of claim 13, wherein said selection vector contains patient condition codes indicative of septic shock.

16. The method of claim 15, wherein the patient condition codes include at least (a) one or more codes specifying one or more organ systems which have failed together with (b) one or more codes specifying an infection.

17. The method of claim 16, wherein the patient condition codes set forth in the selection vector are provided in the format of at least one of ICCS codes, DRG codes, CPT-4 codes, ICD-8 codes, ICD-9 codes, and ICD-10 codes.

18. The method of claim 13, wherein the defined tests include tests indicative of sepsis.

19. The method of claim 18, wherein the defined tests include at least one test that is selected from the group consisting of bacterial tests, acids/base tests, coagulation tests, and fluid sample tests.

20. The method of claim 19, wherein the defined tests include at least one of the following tests: aerobic bacterial culture, anaerobic bacterial culture, and complete blood count.

* * * * *